US009334478B2

(12) United States Patent
West et al.

(10) Patent No.: US 9,334,478 B2
(45) Date of Patent: May 10, 2016

(54) DIFFERENTIATING ES CELLS USING A TENASCIN

(75) Inventors: Michael D. West, Mill Valley, CA (US); Raymond L. Page, Southbridge, MA (US); Hans Schoeler, Muenster (DE); Karen B. Chapman, Mill Valley, CA (US)

(73) Assignee: Advanced Cell Technology, Inc., Worcester, MA (US)

( * ) Notice: Subject to any disclaimer, the term of this patent is extended or adjusted under 35 U.S.C. 154(b) by 949 days.

(21) Appl. No.: 12/322,612

(22) Filed: Feb. 3, 2009

(65) Prior Publication Data

US 2009/0253588 A1 Oct. 8, 2009

Related U.S. Application Data

(63) Continuation of application No. 10/227,282, filed on Aug. 26, 2002, now abandoned.

(60) Provisional application No. 60/314,316, filed on Aug. 24, 2001.

(51) Int. Cl.
*C12N 5/077* (2010.01)
*C12N 5/071* (2010.01)
*G01N 33/50* (2006.01)

(52) U.S. Cl.
CPC .............. *C12N 5/0657* (2013.01); *C12N 5/069* (2013.01); *C12N 5/0652* (2013.01); *G01N 33/5011* (2013.01); *G01N 33/5091* (2013.01); *C12N 2501/115* (2013.01); *C12N 2501/15* (2013.01); *C12N 2501/155* (2013.01); *C12N 2501/23* (2013.01); *C12N 2501/998* (2013.01); *C12N 2506/02* (2013.01); *C12N 2506/03* (2013.01); *C12N 2506/04* (2013.01); *G01N 2333/475* (2013.01); *G01N 2333/52* (2013.01)

(58) Field of Classification Search
None
See application file for complete search history.

(56) References Cited

U.S. PATENT DOCUMENTS

| | | |
|---|---|---|
| 5,004,681 A | 4/1991 | Boyse et al. |
| 5,087,570 A | 2/1992 | Weissman |
| 5,192,533 A | 3/1993 | Elliott et al. |
| 5,639,618 A | 6/1997 | Gay |
| 5,733,727 A | 3/1998 | Field |
| 5,846,720 A | 12/1998 | Foulkes et al. |
| 5,851,832 A | 12/1998 | Weiss |
| 5,922,601 A | 7/1999 | Baetscher |
| 5,928,888 A | 7/1999 | Whitney |
| 5,942,225 A | 8/1999 | Bruder |
| 5,945,577 A | 8/1999 | Stice |
| 5,980,885 A | 11/1999 | Weiss et al. |
| 5,993,387 A | 11/1999 | Moore et al. |
| 6,007,993 A | 12/1999 | Wobus et al. |
| 6,080,576 A | 6/2000 | Zambrowicz |
| 6,123,727 A | 9/2000 | Vacanti |
| 6,136,566 A | 10/2000 | Sands |
| 6,197,575 B1 | 3/2001 | Griffith |
| 6,207,371 B1 | 3/2001 | Zambrowicz |
| 6,214,369 B1 | 4/2001 | Grande |
| 6,280,718 B1 | 8/2001 | Kaufman |
| 6,293,682 B1 | 9/2001 | Kawaguchi |
| 6,808,704 B1 | 10/2004 | Lanza |
| 7,683,159 B2 * | 3/2010 | Chiquet-Ehrismann et al. .................. 530/387.1 |
| 2002/0081311 A1 * | 6/2002 | Shanahan et al. .......... 424/190.1 |
| 2003/0224345 A1 * | 12/2003 | West et al. ........................ 435/4 |
| 2006/0083722 A1 | 4/2006 | Cibelli et al. |
| 2010/0167404 A1 | 7/2010 | West et al. |
| 2010/0173314 A1 * | 7/2010 | Chiquet-Ehrismann et al. . 435/6 |
| 2011/0143441 A1 | 6/2011 | West et al. |
| 2011/0159012 A1 * | 6/2011 | Pesheva .................... 424/172.1 |
| 2011/0171185 A1 | 7/2011 | Klimanskaya et al. |
| 2011/0286978 A1 | 11/2011 | Klimanskaya et al. |
| 2012/0184035 A1 | 7/2012 | Agarwal et al. |
| 2013/0104253 A1 | 4/2013 | Chapman |

FOREIGN PATENT DOCUMENTS

| | | |
|---|---|---|
| CA | 2417356 | 7/2001 |
| CA | 2424062 | 9/2001 |
| CA | 2430653 | 11/2001 |
| EP | 1158044 | 11/2001 |
| EP | 01293561 A1 | 3/2003 |
| WO | WO 98/48001 A1 | 10/1998 |
| WO | WO 99/20741 A1 | 4/1999 |
| WO | WO 99/50426 A1 | 10/1999 |
| WO | WO 00/46348 A1 | 8/2000 |
| WO | WO 01/51616 A2 | 7/2001 |

OTHER PUBLICATIONS

Tosh D et al. 2002. Conversion of pancreatic cells to hepatocytes. Biochem Soc Trans 30:51-55.*
Castro RF et al. 2002. Failure of bone marrow cells to transdifferentiate into neural cells in vivo. Science 297: 1299.*
Mezey E et al. and Castro RF et al. 2003. "Comment on Failure of bone marrow cells to transdifferentiate into neural cells invivo", "Response to Comment on Failure of bone marrow cells to trarlsdifferentiate into neural Cells in vivo." Science299:1184b,c.*
Anderson et al., "Development of Bovine and Porcine Embryonic Teratomas in Athymic Mice," *Animal Reproduction Science* 45:231-240 1996.

(Continued)

*Primary Examiner* — Blaine Lankford
(74) *Attorney, Agent, or Firm* — DLA Piper LLP (US)

(57) ABSTRACT

The invention relates to assays for screening growth factors, adhesion molecules, immunostimulatory molecules, extracellular matrix components and other materials, alone or in combination, simultaneously or temporally, for the ability to induce directed differentiation of pluripotent and multipotent stem cells.

16 Claims, 21 Drawing Sheets

(56) References Cited

OTHER PUBLICATIONS

Anzai et al., "Self-Renewal and Differentiation of a Basic Fibroblast Growth Factor-Dependent Multipotent Hematopoietic Cell Line Derived from Embryonic Stem Cells," *Develop. Growth Differ.* 41:51-58 (1999).
Bain et al., "Embryonic Stem Cells Express Neuronal Properties In Vitro," *Developmental Biology* 168:342-357 (1995).
Baker et al., "In Vitro Preselection of Gene-Trapped Embryonic Stem Cell Clones for Characterizing Novel Developmentally Regulated Genes in the Mouse," *Developmental Biology* 185:201-214 (1997).
Behrendtsen et al., "Metalloproteinases Regulate Parietal Endoderm Differentiating and Migrating in Cultured Mouse Embryos," *Developmental Dynamics* 208:255-265 (1997).
Berger et al., "Self Renewal of Embryonic Stem Cells in the Absence of Feeder Cells and Exogenous Leukaemia Inhibitory Factor," *Growth Factors* 14:145-159 (1997).
Bergers et al., "Extrinsic Regulators of Epithelial Tumor Progression: Metalloproteinases," *Current Opinion in Genetics & Development* 10:120-127 (2000).
Bichet et al., "Oxygen Tension Modulates β-Globin Switching in Embryoid Bodies," *FASEB J.* 13:285-295 (1999).
Biesecker et al., "Interleukin-6 is a Component of Human Umbilical Cord Serum and Stimulates Hematopoiesis in Embryonic Stem Cells In Vitro," *Experimental Hematology* 21:774-778 (1993).
Bonaldo et al., "Efficient Gene Trap Screening for Novel Developmental Genes Using IRESβgeo Vector and In Vitro Preselection," *Experimental Cell Research* 244:125-136 (1998).
Brannen et al., "In Vitro Differentiation of Multipotent Human Neural Progenitors in Serum-Free Medium," *Neuroreport* 11:1123-1128 (2000).
Buttery et al., "Differentiation of Osteoblasts and In Vitro Bone Formation from Murine Embryonic Stem Cells," *Tissue Engineering* 7:89-99 (2001).
Cecconi et al., "Gene Trap: A Way to Identify Novel Genes and Unravel Their Biological Function," *FEBS Letters* 480:63-71 (2000).
Chowdhury et al., "Evidence for the Stochastic Integration of Gene Trap Vectors into the Mouse Germline," *Nucleic Acids Research* 25:1531-1536 (1997).
Cibelli et al., "Parthenogenetic Stem Cells in Nonhuman Primates," *Science* 295:819 (2002).
Couldrey et al., "Disruption of Murine α-Enolase by a Retroviral Gene Trap Results in Early Embryonic Lethality," *Developmental Dynamics* 212:284-292 (1998).
Dunn et al., "A Knock-Out Model of Paroxysmal Nocturnal Hemoglobinuria: Pig-a-Hematopoiesis is Reconstitiued Following Intercellular Transfer of GPI-Anchored Proteins," *Proc. Natl. Acad. Sci. USA* 93:7938-7943 (1996).
Durick et al., "Hunting with Traps: Genome-Wide Strategies for Gene Discovery and Functional Analysis," *Genome Research* 9:1019-1025 (1999).
Dymecki et al., "Using FLP-Recombinase to Characterize Expansion of WNT1-Expressing Neural Progenitors in the Mouse," *Developmental Biology* 201:57-65 (1998).
Eckert et al., "A Colorimetric Immunoassay for the Detection of E-Cadherin and Carcinoembryonic Antigen (CEA) Expression on Human Colon Carcinoma Cell Lines In Vitro," *Cancer Letters* 105:1-4 (1996).
Era et al., "Characterization of Hematopoietic Lineage-Specific Gene Expression by ES Cell In Vitro Differentiation Induction System," *Blood* 95:870-878 (2000).
Evans et al., "Establishment in Culture of Pluripotential Cells from Mouse Embryos," *Nature* 292:154-156 (1981).
Forrester et al., "An Induction Gene Trap Screen in Embryonic Stem Cells: Identification of Genes That Respond to Retinoic Acid In Vitro," *Proc. Natl. Acad. Sci. USA* 93:1677-1682 (1996).
Gmyrek et al., "Normal and Malignant Prostate Epithelial Cells Differ in Their Response to Hepatocyte Growth Factor/Scatter Factor," *American Journal of Pathology* 159:579-590 (2001).
Gossler et al., "Mouse Embryonic Stem Cells and Reporter Constructs to Detect Developmentally Regulated Genes," *Science* 244:463-465 (1989).
Grabel et al., "Using EC and ES Cell Culture to Study Early Development: Recent Observations on Indian Hedgehog and Bmps," *Int. J. Dev. Biol.* 42:917-925 (1998).
El-Hariry et al., "FGF-1 and FGF-2 Modulate the E-Cadherin/Catenin System in Pancreatic Adenocarcinoma Cell Lines," *British Journal of Cancer* 84:1656-1663 (2001).
Henkel et al., "PU.1 But Not ETS-2 is Essential for Macrophage Development From Embryonic Stem Cells," *Blood* 88:2917-2926 (1996).
Hicks et al., "Functional Genomics in Mice by Tagged Sequence Mutagenesis," *Nature Genetics* 16:338-344 (1997).
Hirashima et al., "Maturation of Embryonic Stem Cells Into Endothelial Cells in an In Vitro Model of Vasculogenesis," *Blood* 93:1253-1263 (1999).
Ito et al., "Bimodal Expression of Heparin-Binding EGF-Like Growth Factor in Colonic Neoplasms," *Anticancer Research* 21:1391-1394 (2001).
Kawasaki et al., "Generation of Dopaminergic Neurons and Pigmented Epithelia From Primate ES Cells by Stromal Cell-Derived Inducing Activity," *Proc. Natl. Acad. Sci. USA* 99:1580-1585 (2002).
Kelly et al., "DNA Microarray Analyses of Genes Regulated During the Differentiation of Embryonic Stem Cells," *Molecular Reproduction and Development* 56:113-123 (2000).
Labosky et al., "Mouse Embryonic Germ (EG) Cell Lines: Transmission Through the Germline and Differences in the Methylation Imprint of Insulin-Like Growth Factor 2 Receptor (Igf2r) Gene Compared with Embryonic Stem (ES) Cell Lines," *Development* 120:3197-3204 (1994).
Lanza et al., "Human Therapeutic Cloning," *Nature Medicine* 5:975-977 (1999).
Lee et al., "Efficient Generation of Midbrain and Hindbrain Neurons from Mouse Embryonic Stem Cells," *Nature Biotechnology* 18:675-679 (2000).
Lillien et al., "BMP and FGF Regulate the Development of EGF-Responsive Neural Progenitor Cells," *Development* 127:4993-5005 (2000).
Martin, "Isolation of a Pluripotent Cell Line from Early Mouse Embryos Cultured in Medium Conditioned by Teratocarcinoma Stem Cells," *Proc. Natl. Acad. Sci. USA* 78:7634-7638 (1981).
Matsuda et al., "Glypican-1 Is Overexpressed in Human Breast Cancer and Modulates the Mitogenic Effect of Multiple Heparin-Binding Growth Factors in Breast Cancer Cells," *Cancer Research* 61:5562-5569 (2001).
Matsui et al., "Derivation of Pluripotential Embryonic Stem Cells from Murine Primordial Germ Cells in Culture," *Cell* 70:841-847 (1992).
Murray et al., "The Genes for Leukemia Inhibitory Factor and Interleukin-6 Are Expressed in Mouse Blastocysts Prior to the Onset of Hemopoiesis," *Molecular and Cellular Biology* 10:4953-4956 (1990).
Nichols et al., "Derivation of Germline Competent Embryonic Stem Cells with a Combination of Interleukin-6 and Soluble Interleukin-6 Receptor," *Experimental Cell Research* 215:237-239 (1994).
Odorico et al., "Multilineage Differentiation from Human Embryonic Stem Cell Lines," *Stem Cells* 19:193-204 (2001).
Ogawa et al., "Expression of α4-Integrin Defines the Earliest Precursor of Hematopoietic Cell Lineage Diverged From Endothelial Cells," *Blood* 93:1168-1177 (1999).
Paquin et al., "Oxytocin Induces Differentiation of P19 Embryonic Stem Cells to Cardiomyocytes," *Proc. Natl. Acad. Sci. USA* 99:9550-9555 (2002).
Resnick et al., "Long-Term Proliferation of Mouse Primordial Germ Cells in Culture," *Nature* 359:550-551 (1992).
Reubinoff et al., "Embryonic Stem Cell Lines from Human Blastocysts: Somatic Differentiation In Vitro," *Nature Biotechnology* 18:399-404 (2000).
Reubinoff et al., "Neural Progenitors from Human Embryonic Stem Cells," *Nature Biotechnology* 19:1134-1140 (2001).
Rohwedel et al., "Loss of β$_1$ Integrin Function Results in a Retardation of Myogenic, But an Acceleration of Neuronal, Differentiation of Embryonic Stem Cells in Vitro," *Developmental Biology* 201:167-184 (1998).

(56) References Cited

OTHER PUBLICATIONS

Rohwedel et al., "Muscle Cell Differentiation of Embryonic Stem Cells Reflects Myogenesis In Vivo: Developmentally Regulated Expression of Myogenic Determination Genes and Functional Expression of Ionic Currents," *Developmental Biology* 164:87-101 (1994).
Russ et al., "Identification of Genes Induced by Factor Deprivation in Hematopoietic Cells Undergoing Apoptosis Using Gene-Trap Mutagenesis and Site-Specific Recombination," *Proc. Natl. Acad. Sci. USA* 93:15279-15284 (1996).
Sakamoto et al., "Combined Evaluation of NGF and P75NGFR Expression is a Biomarker for Predicting Prognosis in Human Invasive Ductal Breast Carcinoma," *Oncology Reports* 8:973-980 (2001).
Salminen et al., "Efficient Poly A Trap Approach Allows the Capture of Genes Specifically Active in Differentiated Embryonic Stem Cells and in Mouse Embryos," *Developmental Dynamics* 212:326-333 (1998).
Schuldiner et al., "Effects of Eight Growth Factors on the Differentiation of Cells Derived from Human Embryonic Stem Cells," *Proc. Natl. Acad. Sci. USA* 97:11307-11312 (2000).
Shamblott et al., "Derivation of Pluripotent Stem Cells from Cultured Human Primordial Germ Cells," *Proc. Natl. Acad. Sci. USA* 95:13726-13731 (1998).
Shen et al., "Leukemia Inhibitory Factor is Expressed by the Preimplantation Uterus and Selectively Blocks Primitive Ectoderm Formation In Vitro," *Proc. Natl. Acad. Sci. USA* 89:8240-8244 (1992).
Skarnes et al., "A Gene Trap Approach in Mouse Embryonic Stem Cells: The LacZ Reporter is Activated by Splicing, Reflects Endogenous Gene Expression, and is Mutagenic in Mice," *Genes & Development* 6:903-918 (1992).
Slager et al., "Transforming Growth Factor-β in the Early Mouse Embryo: Implications for the Regulation of Muscle Formation and Implantation," *Developmental Genetics* 14:212-224 (1993).
Stanford et al., "Expression Trapping: Identification of Novel Genes Expressed in Hematopoietic and Endothelial Lineages by Gene Trapping in ES Cells," *Blood* 92:4622-4631 (1998).
Suzuki et al., "Preferential Differentiation of P19 Mouse Embryonal Carcinoma Cells Into Smooth Muscle Cells," *Circ. Res.* 78:395-404 (1996).
Thomson et al., "Isolation of a Primate Embryonic Stem Cell Line," *Proc. Natl. Acad. Sci. USA* 92:7844-7848 (1995).
Thomson et al., "Neural Differentiation of Rhesus Embryonic Stem Cells," *APMIS* 106:149-157 (1998).
Thorey et al., "Selective Disruption of Genes Transiently Induced in Differentiating Mouse Embryonic Stem Cells by Using Gene Trap Mutagenesis and Site-Specific Recombination," *Molecular and Cellular Biology* 18:3081-3088 (1998).
Timeus et al., "FLT-3 and Its Ligand Are Expressed in Neural Crest-Derived Tumors and Promote Survival and Prolifereation of Their Cell lines," *Laboratory Investigation* 81:1025-1037 (2001).
Townley et al., "Rapid Sequence Analysis of Gene Trap Integrations to Generate a Resource of Insertional Mutations in Mice," *Genome Research* 7:293-298 (1997).
Vittet et al., "Embryonic Stem Cells Differentiate In Vitro to Endothelial Cells Through Successive Maturation Steps," *Blood* 88:3424-3431 (1996).
Voss et al., "Efficiency Assessment of the Gene Trap Approach," *Developmental Dynamics* 212:171-180 (1998).
Wiles et al., "Embryonic Stem Cell Development in a Chemically Defined Medium," *Experimental Cell Research* 247:241-248 (1999).
Wiles et al., "Establishment of a Gene-Trap Sequence Tag Library to Generate Mutant Mice from Embryonic Stem Cells," *Nature Genetics* 24:13-14 (2000).
Wiles et al., "Multiple Hematopoietic Lineages Develop from Embryonic Stem (ES) Cells in Culture," *Development* 111:259-267 (1991).
Wirl et al., "Mammary Epithelial Cell Differentiation In Vitro is Regulated by an Interplay of EGF Action and Tenascin-C Downregulation," *Journal of Cell Science* 108:2445-2456 (1995).
Yiu et al., "SPARC (Secreted Protein Acidic and Rich in Cysteine) Induces Apoptosis in Ovarian Cancer Cells," *American Journal of Pathology* 159:609-622 (2001).
Yuen et al., "Generation of a Primitive Erythroid Cell Line and Promotion of its Growth by Basic Fibroblast Growth Factor," *Blood* 91:3202-3209 (1998).
Zambrowicz et al., "Comprehensive Mammalian Genetics: History and Future Prospects of Gene Trapping in the Mouse," *Int. J. Dev. Biol.* 42:1025-1036 (1998).
Zambrowicz et al., "Disruption and Sequence Identification of 2,000 Genes in Mouse Embryonic Stem Cells," *Nature* 392:608-611 (1998).
Zhang et al., "In Vitro Differentiation of Transplantable Neural Precursors from Human Embryonic Stem Cells," *Nature Biotechnology* 19:1129-1133 (2001).
Zhang et al., "Vasculogenesis from Embryonic Bodies of Murine Embryonic Stem Cells Transfected by Tgf-β1 Gene," *Endothelium* 6:95-106 (1998).
Zinyk et al., "Fate Mapping of the Mouse Midbrain-Hindbrain Constriction Using a Site-Specific Recombination System," *Current Biology* 8:665-668 (1998).
Anzai et al., "Self-Renewal and Differentiation of a Basic Fibroblast Growth Factor-Dependent Multipotent Hematopoietic Cell Line Derived from Embryonic Stem Cells," *Dev Growth Differ* 41:51-58 (1999).
Adamson. Cord Blood Stem Cell Banking and Transplantation. Stem Cells vol. 15 pp. 57-61 (1997).
Bradley et al. Stem Cell Medicine Encounters the Immune System. Nature Reviews. vol. 2 pp. 859-871 (2002).
Cibelli, J.B., et al., "Rapid Communication, Somatic Cell Nuclear Transfer in Humans: Pronuclear and Early Embryonic Development," J. Regenerative Medicine, 2:25-32 (2001).
Davies, C.J., "Why is the fetal allograft not rejected?," J. Animal Science, 85(13), E32-35 (2007).
Harris. Experience in Autologous and Allogeneic Cord Blood Banking. Journal of Hematotherapy. vol. 5 pp. 123-128 (1996).
Hua, S., et al., "Development of bovine-ovine interspecies cloned embryos and mitochondria segregation in blastomeres during preimplantation," Animal Reproduction Science, doi:10.1016/j.anireprosci.2007.03.002 (2007).
Kogler et al. HLA typing strategies of cord blood (CB) for unrelated stem cell banking within eurocord. Human Immunology vol. 47 p. 87 (1996).
Schreuder et al. The HLA Directory 1999: A Summary of HLA-A, -B, -C, -DRB1/3/4/5,-DQB1 Alleles and Their Association with Serologically Defined HLA-A, -B, -C, -DR, and -DQ Antigens. Human Immunology. vol. 60 pp. 1157-1181 (1999).
Stem Cells: Scientific Progress and Future Research Directions, Chapter 1: the Stem Cell, http//:stemcells.nih.gov/info/scireport/2001report.htm, pp. 1-4 (2001).
Simerly et al., Molecular Correlates of Primate Nuclear Transfer Failures. Science vol. 300 p. 297 (2003).
Vogel Pioneering Stem Cell Bank Will Soon Be Open for Deposits. Science vol. 297 p. 1784 (2002).
Vogel Misguided Chromosomes Foil Primate Cloning. Science vol. 300 pp. 225-226 (2003).
Wolf Storing Lifeblood. Cord blood stem cell banking. Am J. Nurs. vol. 8 pp. 60-68 (1999).
Westhusin, M.E., et al., "Cloning to Reproduce Desired Genotypes," Theriogenology, 55:35-49 (2001).
Winnier, (1995), Genes and Dev., 9:2105-2116.
Feng et al., BDNF dependence in neuroblastoma. J Neurosci Res. May 15, 2001;64(4):355-63. Abstract only.
Hawighorst et al., Thrombospondin-2 plays a protective role in multistep carcinogenesis: a novel host anti-tumor defense mechanism. EMBO J. Jun. 1, 2001;20(11):2631-40.
Reddy et al., Fluorescence-activated sorting of totipotent embryonic stem cells expressing developmentally regulated lacZ fusion genes. Proc Natl Acad Sci U S A. Aug. 1, 1992;89(15):6721-5.

(56) References Cited

OTHER PUBLICATIONS

Rijkers et al., Sequence and expression pattern of an evolutionarily conserved transcript identified by gene trapping. Biochim Biophys Acta. Jul. 17, 1996;1307(3):294-300. Abstract only.

Sartor et al., Her4 mediates ligand-dependent antiproliferative and differentiation responses in human breast cancer cells. Mol Cell Biol. Jul. 2001;21(13):4265-75.

Shirai et al., A gene trap strategy for identifying the gene expressed in the embryonic nervous system. Zoolog Sci. Apr. 1996;13(2):277-83. Abstract only.

Von Melchner et al., Selective disruption of genes expressed in totipotent embryonal stem cells. Genes Dev. Jun. 1992;6(6):919-27.

Wiles et al., Analysis of factors controlling primary germ layer formation and early hematopoiesis using embryonic stem cell in vitro differentiation. Leukemia. Apr. 1997;11 Suppl 3:454-6. Abstract only.

Yang et al., Trapping genes expressed in the developing mouse inner ear. Hear Res. Dec. 1997;114(1-2):53-61.

Davidson et al., Turning mesoderm into blood: the formation of hematopoietic stem cells during embryogenesis. Curr Top Dev Biol. 2000;50:45-60.

Era et al., Multiple mesoderm subsets give rise to endothelial cells, whereas hematopoietic cells are differentiated only from a restricted subset in embryonic stem cell differentiation culture. Stem Cells. Feb. 2008;26(2):401-11. Epub Nov. 8, 2007.

Ray et al., Flt3 ligand supports the differentiation of early B cell progenitors in the presence of interleukin-11 and interleukin-7. Eur J Immunol. Jul. 1996;26(7):1504-10.

Zhang et al., Mitogenic and anti-proliferative signals for neural crest cells and the neurogenic action of TGF-beta1. Dev Dyn. Mar. 1997;208(3):375-86.

\* cited by examiner

Table 1

| Well Nos. | | | | | | |
|---|---|---|---|---|---|---|
| 1 VEGF-A | 2 LAP | 3 Flt-3 ligand | 4 TGF beta-1 | 5 IGF-1 | 6 PlGF |
| 7 Tie-1R/Fc Chimera | 8 BMP-2 | 9 BMP-4 | 10 BMP-5 | 11 FGF-17 | 12 TGF-alpha |
| 13 Fibronectin (120K) | 14 Tenascin | 15 Merosin | 16 IL-1-alpha | 17 FGF-4 | 18 SCF |
| 19 bFGF | 20 PDGF | 21 PECAM-1 | 22 Anti-FGF-4 antibody | 23 Anti-CRIPTO-1 antibody | 24 BSA/PBS |

Figure 2

Table 2

| I. | | PCR Primers Used | Product Size (bp) | |
|---|---|---|---|---|
| A | GAPDH | NM_002046 | 287 bp | Constitutive Expression |
| B | Oct4 | NM_002701 | 202 bp | -- Undifferentiated cells |
| C | PAX6 | NM_000280 | 501 bp | Ectoderm |
| D | ChAT | XM_046146 | 150 bp | Ectdoderm |
| E | Gamma Enolase | NM_001975 | 320 bp | Ectdoderm |
| F | GATA4 | XM_005135 | 309 bp | Endoderm |
| G | Keratin 19 | NM_002276 | 296 bp | Endoderm |
| H | Nestin | X65964 | 371 bp | Endoderm/Ectoderm |
| I | CD34 | XM_036615 | 246 bp | Mesoderm |
| J | Cardiac Myosin Light Chain I | AF174483 | 203 bp | Mesoderm |
| K | VEGFR-1 | X51602 | 426 bp | Mesoderm |
| L | BMP-RII | NM_001204 | 451 bp | Mesoderm |

Figure 8

Table 3

Figure 13

DIFFERENTIATING ES CELLS USING A TENASCIN

This application is a continuation of U.S. application Ser. No. 10/227,282, published as 2003-0224345, filed Aug. 26, 2002, which claims the benefit of priority from U.S. provisional application No. 60/314,316, filed on Aug. 24, 2001, the disclosures of which are both incorporated by reference in their entirety.

FIELD OF THE INVENTION

The present invention relates to methods for the in vitro culture and differentiation of totipotent, nearly totipotent, and pluripotent cells, and cells derived therefrom. Examples of such cells are embryonic cells, embryonic stem cells, embryonic germ cells, embryoid bodies, inner cell mass cells, formula-derived cells-derived cells, non-embryonic stem cells of embryonic, fetal, and adult animals, such as mesenchymal, hematopoietic, and neuronal stem cells, and cells derived from any of these.

In one aspect, the invention provides efficient, high-throughput assays for screening and identifying chemical and biological agents and physical conditions that may be used to induce and direct the differentiation of totipotent, nearly totipotent, and pluripotent cells, and cells therefrom along particular developmental lineages. Examples of such differentiation-inducing agents and conditions are growth factors, cytokines and extracellular matrix components, cell-cell interactions, environmental conditions (temperature, oxygen pressure, etc.), and other extracellular factors or components, and combinations thereof, to which the target stem cells may be exposed simultaneously or sequentially to induce and direct differentiation.

In another aspect, the invention provides a means of making genetically modified stem cell lines, e.g., gene trap stem cell lines, that facilitate the production, isolation, and therapeutic use of differentiated cell types for cell therapy.

In another aspect, the invention provides a means of producing and isolating particular types of cells for animal testing and cell therapy.

In another aspect, the invention encompasses compositions of growth factors, cytokines, and/or other chemical and biological differentiation-inducing agents, alone or in combination, that are identified by the methods described herein, and their use to direct the development of characterized cell populations and tissues from totipotent, nearly totipotent, and pluripotent cells, and cells therefrom, for use in treatments, transplantation therapies, and drug discovery, including the discovery of novel cancer targets and therapies.

BACKGROUND OF THE INVENTION

The past decade has been characterized by significant advances in the science of cloning, and has witnessed the birth of a cloned sheep, i.e. "Dolly" (Roslin Bio-Med), a trio of cloned goats named "Mira" (Genzyme Transgenics) and over a dozen cloned cattle (Advanced Cell Technology or ACT). Most recent additions to the clone family include pigs (PPL Therapeutics) and mice (University of Hawaii Medical School). Scientists at ACT have also demonstrated successful cross-species nuclear reprogramming by the birth of a cloned guar produced using a bovine recipient oocyte. For example, see U.S. patent application Ser. No. 09/685,062, incorporated by reference herein in its entirety. Furthermore, cloning technology has also advanced such that a mammal may now be cloned using the nucleus from an adult, differentiated cell, which scientists now know undergoes "reprogramming" when it is introduced into an enucleated oocyte. See U.S. Pat. No. 5,945,577, incorporated herein by reference in its entirety.

The showing that an embryo and embryonic stem cells may be generated using the nucleus from an adult differentiated cell has exciting implications for the fields of organ, cell and tissue transplantation. There are currently thousands of patients waiting for a suitable organ donor, who face the problems of both availability and incompatibility in their wait for a transplant. By using a differentiated cell from a patient in need of a transplant to generate embryonic stem cells, and inducing these to differentiate into characterized populations of the cell type required in the transplant, the problem of transplantation rejection and the dangers of immunosuppressive drugs could be precluded. This prospect is now known to many as "therapeutic cloning," or "adult cell reprogramming" so as to distinguish it from "reproductive cloning" and provides a moral boundary as the reach of cloning extends toward the realm of human beings. Lanza et al., September 1999, Human therapeutic cloning, Nat. Med. 5(9): 975-7.

Conscious of the promise of therapeutic cloning, scientists are seeking to understand how to efficiently direct the differentiation of totipotent and pluripotent stem cells into particular cell types and tissues, while at the same time deterring their differentiation into unwanted cells and tissues. Controlled, specific direction of cell differentiation will come from deciphering the factors and signals that control embryonic development. The alternative, e.g., the random differentiation of embryonic cells and subsequent dissection of desired tissues, is both impractical and morally unacceptable for human therapy.

As used herein, a "stem cell" is a cell that has the ability to divide for indefinite periods in culture and to give rise to daughter cells of one or more specialized cell types.

As used herein, an "embryonic stem cell" (ES-cell) is a cell line with the characteristics of the murine embryonic stem cells isolated from morulae or blastocyst inner cell masses (as reported by Martin, G., Proc. Natl. Acad. Sci. USA (1981) 78:7634-7638; and Evans, M. and Kaufman, M., Nature (1981) 292: 154-156) i.e., ES cells are immortal and capable of differentiating into all of the specialized cell types of an organism, including the three embryonic germ layers, all somatic cell lineages, and the germ line.

As used herein, an "embryonic stem-like cell" (ES-like cell) is a cell of a cell line isolated from an animal inner cell mass or epiblast that has a flattened morphology, prominent nucleoli, is immortal, and is capable of differentiating into all somatic cell lineages, but when transferred into another blastocyst typically does not contribute to the germ line. An example in the primate "ES cell" reported by Thomson et al. (Proc. Natl. Acad. Sci. USA. (1995) 92:7844-7848)

As used herein, "inner cell mass-derived cells" (ICM-derived cells) are cells derived from isolated ICMs or morulae before they are passaged to establish a continuous ES or ES-like cell line.

As used herein, an "embryonic germ cells" (EG cells) is a cell of a line of cells obtained by culturing primordial germ cells in conditions that cause them to proliferate and attain a state of differentiation similar, though not identical to embryonic stem cells. Examples are the murine EG cells reported by Matsui, et al, 1992, Cell 70: 841-847 and Resnick et al, Nature. 359: 550-551. EG cells can differentiate into embryoid bodies in vitro and form teratocarcinomas in vivo (Labosky et al., Development (1994) 120:3197-3204). Immunohistochemical analysis demonstrates that embryoids produced by EG cells contain differentiated cells that are derivatives of all three embryonic germ layers (Shamblott et al., Proc. Nat. Acad. Sci. U.S.A. (1998) 95:13726-13731).

As used herein, a "totipotent" cell is a stem cell with the "total power" to differentiate into any cell type in the body, including the germ line following exposure to stimuli like that normally occurring in development. An example of such a cell is an ES cell, an EG cell, an ICM-derived cell, or a cultured cell from the epiblast of a late-stage blastocyst.

As used herein, a "nearly totipotent cell" is a stem cell with the power to differentiate into most or nearly all cell types in the body following exposure to stimuli like that normally occurring in development. An example of such a cell is an ES-like cell.

As used herein, a "pluripotent cell" is a stem cell that is capable of differentiating into multiple somatic cell types, but not into most or all cell types. This would include by way of example, but not limited to, mesenchymal stem cells that can differentiate into bone, cartilage and muscle; hemotopoietic stem cells that can differentiate into blood, endothelium, and myocardium; neuronal stem cells that can differentiate into neurons and glia; and so on.

As used herein, "differentiation" refers to a progressive, transforming process whereby a cell acquires the biochemical and morphological properties necessary to perform its specialized functions.

As used herein, a "marker" is a characteristic or feature of a cell that is indicative of a particular cellular state. Typically, a marker is a biochemical entity that changes state in a detectable manner when the cell enters or leaves a particular state. For example, a marker may be a DNA sequence encoding a product that is detectable (e.g., a specific mRNA, or a fluorescent or antigenic protein) or has detectable activity (e.g., a protein conferring antibiotic resistance or a chromogenic enzyme such as lacZ). When copies of the marker DNA sequence are randomly inserted into the genomic DNA of a cell, some copies may be inserted proximal to a promoter in the correct orientation and in-frame such that activation of the promoter results in transcription of the marker DNA sequence and synthesis of the detectable product that it encodes. Detection of the marker then identifies the cell as one that contains the marker gene in a transcriptionally active genetic locus. The term "marker" as used herein may refer to a marker gene, or to a marker RNA or protein encoded by such a gene.

Directed Differentiation of Stem Cells

Totipotent and nearly totipotent embryo-derived stem cells can be induced to differentiate into a wide variety of cell types, some of which are needed for cell therapy. For example, Anderson et al. demonstrated that inner cell masses (ICM) and embryonic discs from bovine and porcine blastocysts will develop into teratomas containing differentiated cell types from ectodermal, mesodermal and endodermal origins when transplanted under the kidney capsule of athymic mice. *Animal Repro. Sci.* 45: 231-240 (1996). Thomson et al. reported that primate ES cells are capable of differentiating into trophoblast and derivatives of the three embryonic germ layers, and describe transplanting primate ES cells into muscles of immunodeficient mice to generate teratomas that also contain cells of the three embryonic germ layers, including tissues resembling neural tube, embryonic ganglia, neurons, and astrocytes (APMIS (1998) 106(1):149-156). ES cells of mice (Lee et al., Nature Biotech. (2000) 18:675-679), cynomolgus monkeys (*Macaca fascicularis*) (Cibelli et al., Science (2002) 295:819), and humans (Zhang et al., Nature Biotech. (2001) 19:1129-1133) can be cultured in vitro to generate embryoids that contain cells of all three germ layers, including neural precursor cells that test positive for nestin (an intermediate filament protein produced in the developing central nervous system and widely used as a marker for proliferating neural progenitor cells in the nervous system). Pluripotent stem cells can be isolated from ES and EG cell-derived teratomas and embryoids and exposed to conditions that induce them to differentiate into specific cell types that are useful for cell therapy. For example, nestin-positive neural stem cells isolated from human embryoids can be cultured under conditions that induce their differentiation into the three major cell types of the central nervous system (see Zhang et al. (2001) p. 1130).

The foregoing reports describe the derivation of precursor or differentiated cells that appear to arise randomly or spontaneously in embryoids and teratomas generated from totipotent ES and EG cells. Production of a characterized population of differentiated cells by these methods therefore requires isolating the differentiated cells of interest, or their precursors, from other types of cells in an embryoid or teratoma. Presently, there is strong interest in identifying chemical, biological, and physical agents or conditions that induce totipotent or nearly totipotent cells such as ES and EG cells to differentiate directly into the desired differentiated cells, in order to develop efficient methods for producing characterized populations of differentiated cells that are useful for cell therapy.

In U.S. Pat. No. 5,733,727, Field described plating murine ES cells onto uncoated petri dishes and culturing them in medium that is free of leukemia inhibitory factor (LIF), an inhibitor of differentiation, to generate patches of cardiomyocytes that exhibit spontaneous contractile activity (col. 12, lines 63-67). Field also described a useful method for purifying cells induced to differentiate into a specific cell type from other types of cells present in the culture: the parental ES cells are cotransfected with a pGK-HYG (hygromycin) plasmid and a plasmid containing a MHC-neo$^r$ fusion gene—an α-cardiac myosin heavy chain (MHC) promoter operably linked to a neo$^r$ gene that confers resistance to neomycin. The pGK-HYG plasmid provides selection for transfected cells, while the MHC-neo$^r$ gene permits a second round of selection of the differentiated cells—incubation in the presence of G418 eliminates non-cardiomyocyte cells in which the MHC promoter is inactive (see col. 12, lines 63-67). The disclosure of U.S. Pat. No. 5,733,727 is incorporated herein by reference in its entirety.

Schuldiner et al. described a systematic approach to analyzing the differentiation of ES-derived cells in response to different growth factors. They cultured human ES cells to generate embryoids, dissociated the embryoids and cultured the cells as a monolayer in the presence of one of eight different growth factors. The differentiation induced by the growth factors was examined by monitoring changes in the cells' morphologies, and by RT-PCR (reverse transcription—polymerase chain reaction) analysis of the expression of a panel of 24 cell-specific genes in the parental ES cells, embryoid cells, and the dissociated embryoid cells cultured in the presence or the absence of one of the eight growth factors. Schuldiner et al. reported that each of the growth factors appeared to induce expression of different subset of the 24 marker genes that were analyzed; and that the growth factor-treated cultures were relatively homogenous, often containing only one or two cell types, whereas the dissociated embryoid cells cultured in the absence of a growth factor spontaneously differentiated into many different types of colonies. The growth factors appeared to act more by inhibiting than by inducing the differentiation of specific cell types, and none of the growth factors tested directed a completely uniform and singular differentiation of cells, and suggesting that direction of formation of specific cell types will require combinations of factors including those that inhibit undesired pathways and those that induce differentiation of specific cell types. (See Proc. Natl. Acad. Sci. USA (2000) 97(21): 11307-12). Paquin et al. described culturing murine P19 ES cells under conditions resulting in formation of aggregates of cells, some of which differentiated into beating cardiomyocytes (Proc. Nat. Acad. Sci. (2002) 99(14):9550-9555). Reubinoff et al. described manipulating the conditions in which human ES cells were cultured to induce their differentiation directly into neural precursors that could then be induced to differentiate into derivatives of the three neural lineages, neuronal cells, glial cells, and astrocytes (Nature Biotechnology (2001) 19:1134-1139). Kelly et al. have shown that changes in gene expression in ES cells in response to retinoic acid are highly reproducible (Mol. Reprod. Dev. (2000) 56(2): 113-23), a result that implies that growth factor-directed differentiation of embryonic cells is dependably reproducible.

Other groups have had success in using a negative approach to identify factors necessary for the differentiation of ES cells into certain cell types. For instance, Henkel and colleagues reported that the transcription factor PU.1 is essential for macrophage development from embryonic stem cells by showing that ES cells containing a homozygous knockout of the PU.1 gene failed to differentiate into macrophages (see Henkel et al., Blood (1996) 88(8): 2917-26). Similarly, Dunn and colleagues demonstrated that knockout embryoid bodies containing a targeted disruption of the phosphatidylinositol glycan class A (Pig-a) gene failed to develop secondary hematopoietic colonies and demonstrated a grossly aberrant morphology (see Dunn et al., Proc. Natl. Acad. Sci. USA (1996) 93(15): 7938-43).

Directed differentiation has also been demonstrated successfully in pluripotent adult stem cells. For instance, U.S. Pat. No. 5,942,225 to Bruder et al. describes the lineage-directed induction of human mesenchymal stem cell differentiation by exposing such stem cells to a bioactive factor or combination of factors effective to induce differentiation either ex vivo or in vivo. Mesenchymal stem cells are more differentiated than embryonic stem cells and only differentiate into lineages including osteogenic, chondrogenic, tendonogenic, ligamentogenic, myogenic, marrow stromagenic, adipogenic and dermogenic lineages. Similarly, U.S. Pat. No. 5,851,832 to Weiss et al. describes the in vitro proliferation and differentiation of neural stem cells following exposure of the cells to various growth factors. Such stem cells are limited in their differentiation potential, producing only neurons and glial cells, including astrocytes and oligodendrocytes (see also Brannen et al., Neuroreport (2000) 11(5): 1123-8; Lillien et al., Dev. (2000) 127: 4993-5005).

The studies described above have shown that totipotent, nearly totipotent, and pluripotent stem cells can be induced to differentiate into specific cell types by manipulating the concentration of growth factors and cytokines in the medium in which they are cultured. Other examples of growth factor-induced differentiation include induction of stem cells to become macrophages, mast cells or neutrophils by IL-3 (Wiles et al., Development (1991) 111:259-267); the direction of cells to the erythroid lineage by IL-6 (Biesecker et al., Exp. Hematol. (1993) 21: 774-778); induction of neuronal differentiation by retinoic acid (Slager et al., Dev. Genet. (1993) 14: 212-224; Bain et al., Dev. Biol. (195) 168:342-357); and induction of myogenesis by transforming growth factor (Rohwedel et al., Dev. Biol. (1994) 164, 87-101). In the latter examples, the inducing agents were not directly applied to ES cells or cells directly derived from the embryo, but rather to aggregates of ES cells or to embryoids.

In addition to manipulating the concentration of growth factors and cytokines, totipotent and pluripotent stem cells may be induced to differentiate into specific cell types by co-culturing them with cells of a different type. For example, Kaufman et al. (U.S. Pat. No. 6,280,718) showed that human ES cells differentiate into hematopoietic precursor cells when cultured on a feeder cell layer of mammalian stromal cells (see col. 5, line 7, to col. 6, line 26). The disclosure of U.S. Pat. No. 6,280,718 is incorporated herein by reference in its entirety. Similarly, Kawasaki et al. have induced the differentiation of cynomolgus monkey ES cells into dopaminergic neurons and pigmented epithelial cells by culturing them on a feeder layer of murine stromal cells (see Proc. Natl. Acad. Sci. USA (2002) 99(3):1580-85).

As shown by the reports described above, research groups' attempts to identify the agents or conditions that induce the differentiation of totipotent and pluripotent stem cells into specific cell types generally involve exposing the stem cells to one or two solutions containing a relatively small number of growth factors or cytokines, and monitoring to see if the stem cells differentiate to acquire a morphology and/or to express a marker gene that is characteristic of a specific cell type.

At present, there is a need for a systematic, large-scale, screening assay to efficiently identify the combinations of biological, biochemical, and physical agents or conditions that act, simultaneously or sequentially, to induce the differentiation of totipotent, nearly totipotent, or pluripotent stem cells into a large number of different, specific cell types.

Also needed are means for efficiently identifying, analyzing and characterizing marker genes and gene products that specifically mark key regulatory steps associated with the induction of differentiation of such stem cells into each of the important specific cell types.

There is also a need for an efficient means for producing and purifying characterized populations of differentiated cells that are suitable and useful for cell therapy, and for testing these in animal models.

The present invention accomplishes these ends, without being limited thereto.

Differentiation Pathways in Oncogenesis

Many molecular events in oncogenesis are a recapitulation or mutation of events that normally occur in differentiation. In this respect, in many cases oncogenesis reflects a reversal of terminal differentiation utilizing, at least in part, pathways used in normal development. Control of cell growth and differentiation by extracellular signals often involves growth factor binding to high affinity transmembrane receptors such as the receptor tyrosine kinases (RTKs) For example, Recently Sakamoto et al, 2001, (Oncol. Rep. 8: 973-80) reported that nerve growth factor and its low-affinity receptor p75NGFR play a role in breast cancer, Gmyrek et al, 2001 (Am. J. Pathol. 159: 579-90) described the role of hepatocyte growth factor/scatter factor ((HGF/SF) that binds the Met receptor and promotes the differentiation of epithelial cells in prostate, kidney, and hepatocellular carcinoma, similarly, mutations in the Ret receptor has been implicated in multiple endocrine neoplasias, the kit receptor in mastocytomas and gastrointestinal tumors, the Flt-3 ligand that plays a role in hematopoietic differentiation has been implicated in neural crest-derived tumors (Timeus et al, 2001, Lab. Invest. 81: 1025-1037), FGF-1 and -2 in pancreatic malignancy (El-Hariry et al, 2001, Br. J. Cancer, 84: 1656-63), HB-EGF in colon cancer (Ito et al, 2001, Anticancer Res. 21: 1391-4), Oncostatin M in breast cancer, Glypicans in breast cancer (Matsuda et al, 2001, Cancer Res. 61: 5562-9), and Yiu et al, 2001 (Am. J. Pathol. 159: 609-22) described the role of the extracellular matrix component SPARC in the apoptosis pathway in ovarian cancer. These only a few examples of the many extracellular components that are important in the differentiation of a particular cell type, and also play a role in cancer. Surprisingly, few assays for antitumor agents, or assays for novel targets in cancer therapy have been based on the identification of factors influencing early differentiation pathways. The present invention also provides means for efficiently screening many combinations of biological, biochemical, and physical agents or conditions to identify treatments that may induce cancerous cells to undergo differentiation and inhibit their proliferation.

BRIEF DESCRIPTION OF THE FIGURES

FIG. 2: Table 1 identifies the factors added to each of the wells of the duplicate 24-well plates of Example 2.

FIG. 8: Table 2 identifies the primers that were used to detect expression of cell type-associated genes by RT-PCR, and the expected sizes of the DNA fragments produced by the RT-PCR reactions.

FIG. 12A (on left): The arrowhead points to a beating myocardial cell.

FIG. 12B (on right): The arrowhead points to an endothelial cell adjacent to myocardial cells.

Figure 13:
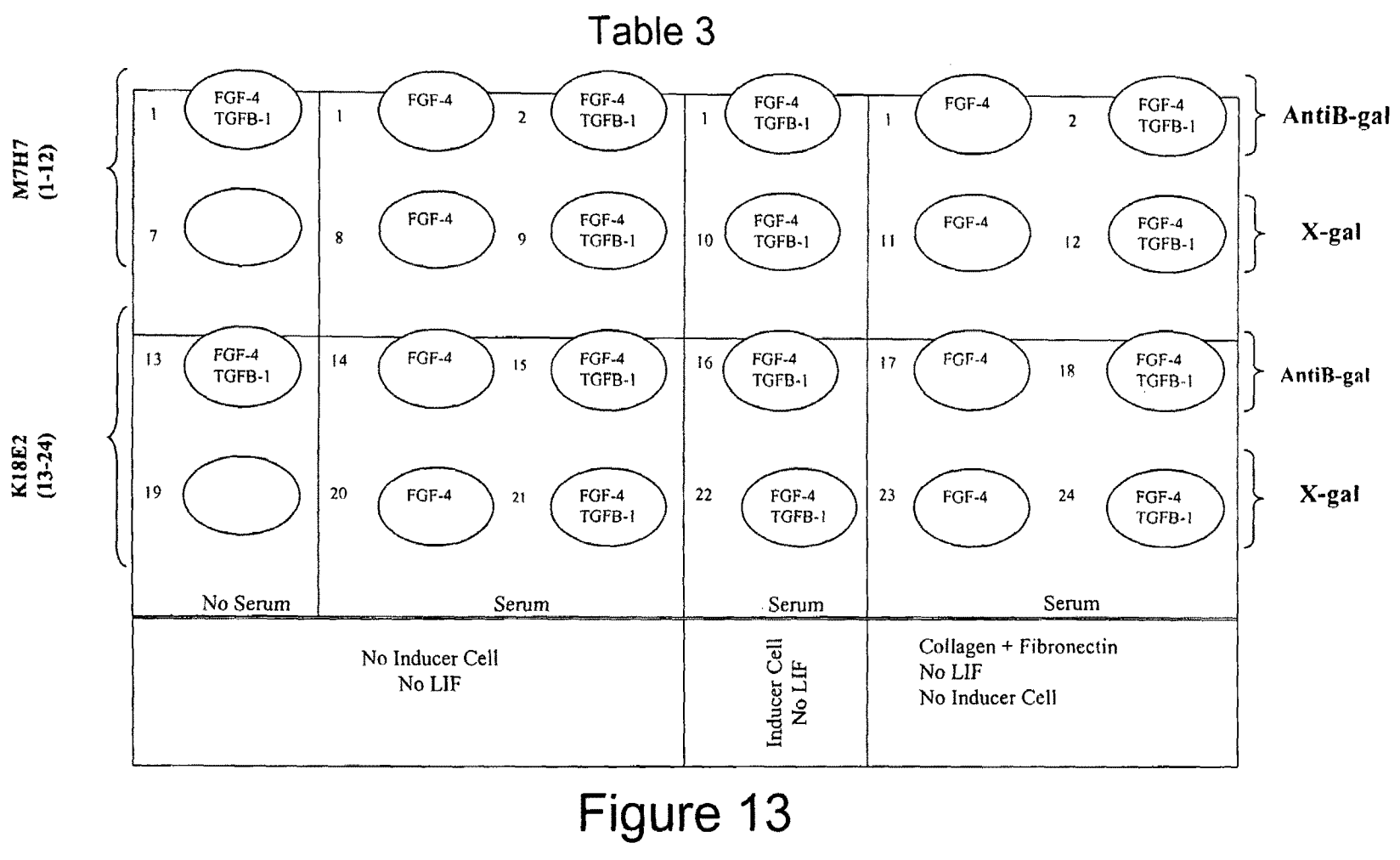

FIG. 13: Table 3 identifies the combinations of putative differentiation-inducing agents added to the wells of the 24 well plates in which murine ES cells were cultured as described in Example 6.

DESCRIPTION OF THE INVENTION

Figure 1:
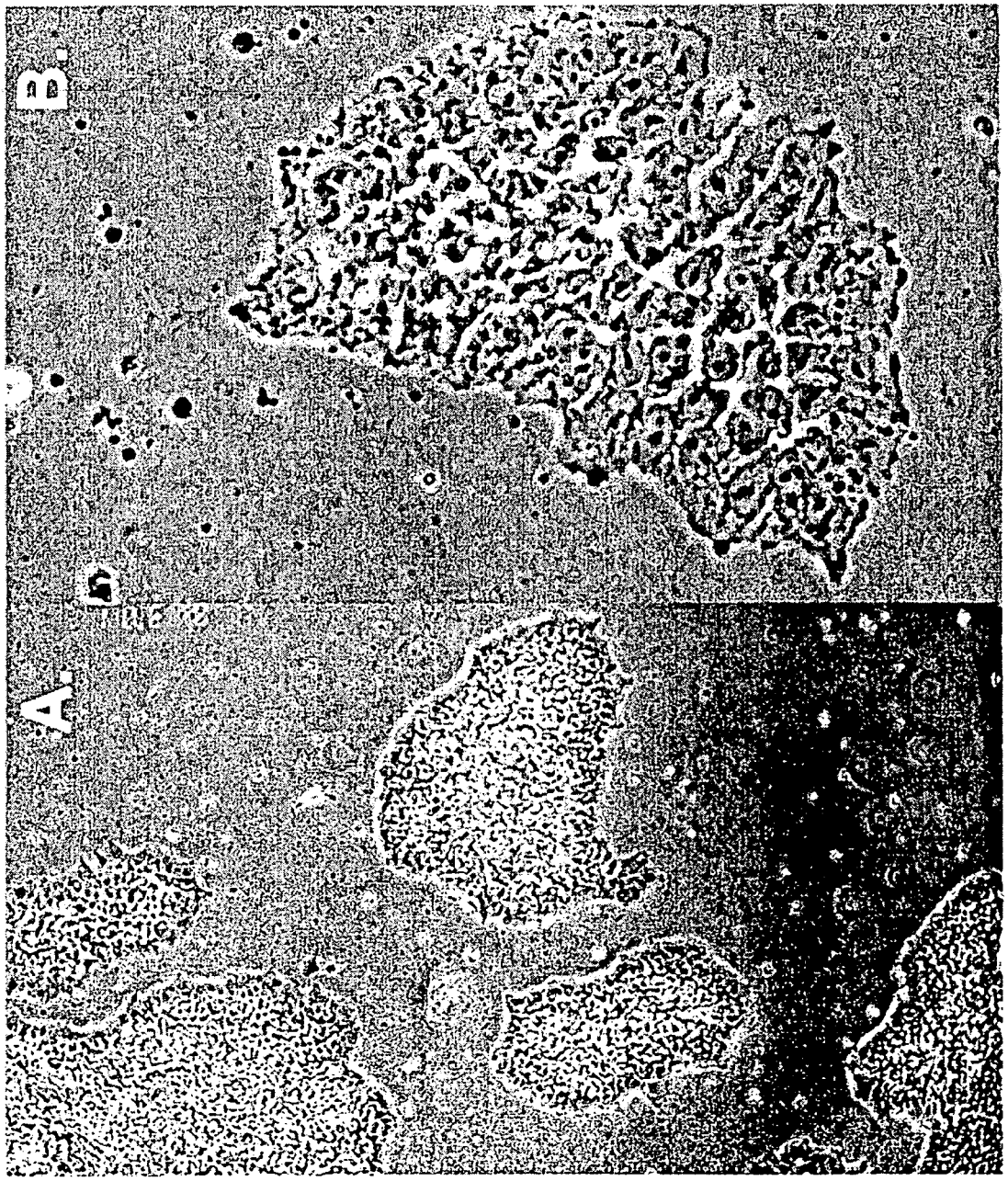
FIG. 1A is a photograph that shows primate Cyno-1FF ES-like cells conditioned to grow on tissue culture dishes without feeder fibroblasts (10×).
FIG. 1B shows Cyno-1FF cells at a higher magnification, showing the typical morphology of ES-like cells (40×).

An object of the present invention is to provide a high-throughput screening assay for efficiently identifying chemical, physical, and biological agents and/or conditions, and combinations of such agents and/or conditions, that induce or direct the differentiation of totipotent, nearly totipotent, or pluripotent stem cells, and cells therefrom into a large number of different, specific cell types, including cell types that are useful for cell therapy.

Another object of the present invention is to provide efficient means for identifying and characterizing biochemical markers in cells that are associated with the series of regulatory steps or "nodes" in the branching pathways by which totipotent, nearly totipotent, or pluripotent stem cells, and cells therefrom differentate into a large number of different, specific cell types, including cell types that are useful for cell therapy.

Another object of the present invention is to provide efficient means for producing totipotent, or pluripotent stem cells, and cells therefrom that are genetically modified to facilitate the production, isolation, and therapeutic use of differentiated cell types for cell therapy.

In one aspect, the invention includes assays for identifying chemical and biological agents and physical conditions which may be used to direct the differentiation of totipotent, nearly totipotent, and pluripotent cells, and cells therefrom along a particular developmental lineage. Examples of such differentiation-inducing chemical and biological agents and physical conditions are growth factors, cytokines and extracellular matrix components, cell-cell interactions, environmental conditions (temperature, oxygen pressure, etc.), and other extracellular factors or components, and combinations thereof, to which the target cells may be exposed simultaneously or sequentially. Examples of biological agents that can be used as putative differentiation-inducing agents include living or dead cells of all types, as well as portions or fractions of any cells, including compositions comprising organelles, internal and external cell membranes, membrane-associated proteins, soluble proteins, protein complexes, complexes of proteins and other molecular classes, including lipids, carbohydrates, and nucleic acids, etc. Methods for fractionating cells to prepare fractions that may be used as biological agents that are putative differentiation-inducing agents are well known. Other biological agents useful as differentiation-inducing agents are cell culture-conditioned medium, and extracts or fractions of natural or artificial tissues.

In another aspect, the invention provides means of making gene trap stem cell lines that have DNA encoding a detectable marker inserted as a marker gene in a genetic locus that is activated when the cells differentiate. The DNA encoding the gene trap marker may be inserted in-frame with correct orientation at a site such that it is expressed and the marker is produced when the genetic locus in which it is inserted is activated. The inserted coding sequence then operates as a marker permitting detection of the differentiation of the stem cells. DNA encoding beta-galactosidase is an example of a commonly used gene trap marker suitable for the invention.

Another aspect of the present invention to provide efficient means for producing totipotent, or pluripotent stem cells, and cells therefrom that are genetically modified to facilitate the production, isolation, and therapeutic use of differentiated cell types for cell therapy.

In another aspect, the invention provides a means of isolating particular types of cells for animal testing and cell therapy.

In another aspect, the invention encompasses compositions of growth factors, cytokines, and/or other differentiation-inducing agents, alone or in combination, that are identified by the methods described herein, and their use to direct the development of characterized cell populations and tissues from totipotent, nearly totipotent, and pluripotent cells, and cells therefrom, for use in treatments, transplantation therapies, and drug discovery, including the discovery of novel cancer targets and therapies.

Nuclear transfer is a useful method for generating totipotent, nearly totipotent, or pluripotent stem cells that can be used in the methods of the invention for screening agents and conditions that induce and direct stem cells differentiation. The nuclear transfer methods useful for generating stem cells for the screening methods of the present invention are the same as those for generating totipotent, nearly totipotent, or pluripotent stem cells that differentiate into cells that are useful for cell therapy. Such methods are described in the co-pending International Application filed on Jul. 18, 2002, based on U.S. Provisional Application No. 60/305,904 and assigned to Advanced Cell Technology, the contents of which are incorporated herein in their entirety, nuclear transfer can also be used to generate Stem Cells:

The assays of the invention may be performed with any appropriate totipotent, nearly totipotent, or pluripotent stem cells, and cells therefrom. Such cells include inner cell mass (ICM) cells, embryonic stem (ES) cells, embryonic germ (EG) cells, embryos consisting of one or more cells, embryoid body (embryoid) cells, morula-derived cells, as well as multipotent partially differentiated embryonic stem cells taken from later in the embryonic development process, and also adult stem cells, including but not limited to nestin positive neural stem cells, mesenchymal stem cells, hematopoietic stem cells, pancreatic stem cells, marrow stromal stem cells, endothelial progenitor cells (EPCs), bone marrow stem cells, epidermal stem cells, hepatic stem cells and other lineage committed adult progenitor cells.

Totipotent, nearly totipotent, or pluripotent stem cells, and cells therefrom, for use in the present invention can be obtained from any source of such cells. One means for producing totipotent, nearly totipotent, or pluripotent stem cells, and cells therefrom, for use in the present invention is via nuclear transfer into a suitable recipient cell as described in U.S. Ser. No. 09/655,815, the disclosure of which is incorporated herein by reference in its entirety. Nuclear transfer using an adult differentiated cell as a nucleus donor facilitates the recovery of transfected and genetically modified stem cells as starting materials for the present invention, since adult cells are often more readily transfected than embryonic cells.

The methods of the invention may be performed with totipotent, nearly totipotent, or pluripotent stem cells, and cells therefrom, of any animal species, including but not limited to human and non-human primate cells, ungulate cells, rodent cells, and lagomorph cells. Primate cells with which the invention may be performed include but are not limited to cells of humans, chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Rabbits are an example of a lagomorph species with which the invention may be performed.

For example, the methods of the invention may be performed with murine ES cells lines, or with primate ES or EG cell lines. An example of a primate stem cell line with which the methods of the invention may be performed is the totipotent non-human primate stem cell line Cyno-1, which was isolated from the inner cell mass of parthenogenetic Cynomologous monkey embryos and is capable of differentiating into all the cell types of the body. Cibelli et al. (Science (2002) 295:819).

Genetic Modification of Stem Cells:

Some embodiments of the invention use stem cells that have been genetically modified, or a library of such stem cells. For example, screening to identify agents or conditions that induce stem cells to differentiate into a large number of different, specific cell types can be carried out efficiently in a high-throughput manner using gene trap stem cell libraries, as discussed below.

After employing the screening assays of the invention to identify agents or conditions that induce stem cells to differentiate into desired cell types, e.g., cells that are useful for cell therapy, it is an aspect of the present invention to genetically modify the stem cells (either the gene trap cells, or unmodified ES cells of the same type), to facilitate the production, isolation, and therapeutic use of differentiated cell types for cell therapy.

For example, stem cells that give rise to differentiated cells for cell therapy can be genetically modified by correcting congenital mutations, or by introducing, altering, or deleting one or more genomic DNA sequences to provide therapeutic benefit to the patient receiving the cell transplant (gene therapy).

Nuclear transfer using an adult differentiated cell as a nucleus donor facilitates the recovery of transfected and genetically modified stem cells as starting materials for the present invention, since adult cells are often more readily transfected than embryonic cells.

In some instances, these cells may be genetically modified to express a selectable marker, or engineered with a genetic modification that renders the cells lineage defective. For instance, selectable markers may be utilized to further purify specific cell types from samples of differentiated cells derived using the methods reported herein. Such methods would include the use of positive selection wherein the selectable marker is, for example, the neomycin or hygromycin resistance gene. This allows the cells that have not differentiated into the chosen cell type to be killed by G418 in the case of neomycin resistance. Alternatively, the specific promoter may drive other selection systems such as a cell surface antigen that allows, for instance, the isolation of the chosen cells using flow cytometry. Alternatively, cells may be modified with a suicide gene operably expressed from a tissue-specific or lineage specific promoter, i.e., as a supplement to the compounds and combinations identified using the methods disclosed herein, in order to facilitate the recovery of desirable cells and tissues.

Culturing on Serum-Free Medium:

Embryonic cells have the propensity to differentiate randomly and rapidly upon removal of LIF (leukemia inhibitory factor), and the feeder cells normally used to maintain embryonic cells may produce growth factors or other compounds that could complicate results (see Reubinoff et al., Nature Biotech. (2000) 18(4): 399-404). Thus, an embodiment of the screening assays may include adapting the cells to a serum-free medium or, in the case of some embryo-derived cells, to growth in the absence of a fibroblast feeder layer in which they do not necessarily need to proliferate, but in which they will survive and remain responsive to the test compounds applied. Different serum-free media are known in the art and may be tested and used with any given cell line in the methods disclosed herein. For instance, in evaluating the in vitro growth and differentiation of multipotent stem cells, U.S. Pat. No. 5,851,832 (herein incorporated by reference) describes the use of a serum-free medium composed of DMEM/F-12 (1:1) including glucose (0.6%), glutamine (2 μM), sodium bicarbonate (3 mM), and HEPES. A defined hormone and salt mixture was used in place of serum. Wiles et al. describe a serum-free chemically defined medium (CDM) for studying ES cell differentiation that fails to support spontaneous differentiation of ES cells while still permitting the evaluation of differentiation in response to exogenous factors (see Wiles et al., Exp. Cell Res. (1999) 247(1): 241-8). According to this group, in the absence of LIF and a feeder layer, ES cells typically differentiate rapidly, forming predominantly endoderm, mesoderm and hematopoietic cells. However, in CDM, the cells still lose their ES cell phenotype but fail to form mesoderm. Rather, the cells enter a neuroectoderm commitment up to a limited point that is thought to be a type of "default" pathway that occurs in the absence of any exogenous differentiation signals.

Nichols and colleagues report the maintenance of ES cells in the absence of a feeder layer with a combination of IL-6 plus soluble IL-6 receptor. Nichols et al., 1994, Derivation of germ-line competent embryonic stem cells with a combination of interleukin-6 and soluble interleukin 6 receptor, Exp. Cell Res. 215(1): 237-9. However, this combination activates the same signaling processes as does LIF, so this medium may not be suitable to study the putative differentiation inducing factors. Although, it has been reported that ES cells do differentiate in the presence of LIF (see Shen et al., Proc. Natl. Acad. Sci. USA (1992) 89: 8240-44). Furthermore, in vivo, LIF is present at the blastocyst stage of development (Murray et al., Mol. Cell. Biol. (1990) 10: 4953-56). Thus, the response of ICM cells toward LIF may be regulated temporally and/or spatially in order to permit development to proceed.

Another group has isolated an ES cell line that is feeder cell-independent and LIF-independent, and yet still contributes to all embryonic germ layers when placed in the environment of a developing embryo (Berger et al., Growth Factors (1997) 14(2-3): 145-59). However, the cells were isolated by selection through passage so the mutations that contribute to this self renewal ability are not known. Nevertheless, one can isolate a similar line of ES cells to be used in the present invention as an alternative to developing a specific maintenance medium.

Another option is to maintain the embryonic cells on a feeder layer in the presence of LIF until the time of the assay. In their evaluation of the affects of eight different growth factors on ES cells, Schuldiner and colleagues transferred the ES cells to gelatin coated plates for five days to allow for initial differentiation as aggregates, then replated the cells as a monolayer wherein the cells were exposed to the test growth factors. See Schuldiner et al., 2000, supra. A similar approach is commonly used to direct mouse ES cells in to specific cell types, such as nerve cells or muscle cells (Slager et al., 1993, supra; Bain et al., 1995, supra; and Rohwedel et al., 1994, supra). However, Schuldiner also reported that the cells spontaneously differentiated into all different cell types in the absence of any tested growth factor, wherein the samples that were treated with specific growth factors were more homogenous than the untreated control. Thus, it may be for any particular assay that the combination of compounds tested will achieve the directed differentiation desired in the absence of specific media formulations that seek to deter differentiation. Indeed, researchers are finding that the process of directed differentiation may involve compounds that inhibit certain developmental pathways either alone or in combination with inductive compounds.

Inducers of Differentiation:

The methods of the invention may be used to screen a wide variety of compounds and culture conditions to determine their effect on the differentiation of stem cells. For instance, the methods may be performed with one or more putative differentiation-inducing compounds selected from the group consisting of growth factors, cytokines, factors involved in cell-to-cell interactions, adhesion molecules, extracellular matrix components, media components, environmental conditions, etc. Media components suitable for use include both identified and unidentified media components; for example, unidentified present in medium conditioned by cell culture may be used as an inducer of differentiation. The present invention includes screening to identify biological compositions that comprise one or more unidentified agents that induce differentiation, and using known fractionation and assay methods to isolate the active agent(s).

The methods and assays of the present invention may also be used to analyze the differentiation of cells in response to materials isolated from early stage fetuses or factors or homogenates or isolated differentiated cells derived therefrom. Other cells, including primary cells and tissues or isolated cell lines, may also be screened for their potential to induce the differentiation of cells according to the disclosed methods and assays.

Examples of growth factors, chemokines, and cytokines that may be tested in the disclosed assays include but are not limited to the Fibroblast Growth Factor family of proteins (FGF1-23) including but not limited to FGF basic (146 aa) and it's variants, FGF acidic, the TGF beta family of proteins including but not limited to TGF-beta 1, TGF-beta 2, TGF-beta sRII, Latent TGF-beta, the Tumor necrosis factor (TNF) superfamily (TNFSF) including but not limited to TNFSF1-18, including TNF-alpha, TNF-beta, the insulin-like growth factor family incuding but not limited to IGF-1 and their binding proteins including but not limited to IGFBP-1, II-1 R rp2, IGFBP-5, IGFBP-6, the matrix metalloproteinases including but not limited to MMP-1, CF, MMP-2, CF, MMP-2 (NSA-expressed), CF, MMP-7, MMp-8, MMP-10, MMP-9, TIMP-1, CF, TIMP-2 and other growth factors and cytokines including but not limited to PDGF, Flt-3 ligand, Fas Ligand, B7-1 (CD80), B7-2(CD86), DR6, IL-13 R alpha, IL-15 R alpha, GRO beta/CXCL2 (aa 39-107), IL 1-18, 11-8/CXCL8, GDNF, G-CSF, GM-CSF, M-GSF, PDGF-BB, PDGF-AA, PDGF-AB, IL-2 sR alpha, IL-2 sR beta, Soluble TNF RII, IL-6 sR, Soluble gp130, PD-ECGF, IL-4 sR, beta-ECGF, TGF-alpha, TGF-beta sRII, TGF-beta 5, LAP (TGF-beta 1), BDNF, LIF sR alpha, LIF, KGF/FGF-7, Pleiotrophin, ENA-78/CXCL5, SCF, beta-NGF, CNTF, Midkine, HB-EGF, SLPI, Betacellulin, Amphiregulin, PIGF, Angiogenin, IP-10/CXCL10, NT-3, NT4, MIP-1 alpha/CCL3, MIP-1 beta/CCL4, 1-309/CCL1, GRO alpha/CXCL1, GRO beta/CXCL2, GRO gamma/CXCL3, Rantes/CCL5, MCP-1/CCL2, MCP-2/CCL8, MCP-3/CCL7, IFN-gamma, Erythropoietin, Thrombopoietin, MIF, IGF-I, IGF-II, VEGF, HGF, Oncostatin M, HRG-alpha (EGF Domain), TGF-beta 2, CNTF R alpha, Tie-2/Fc Chimera, BMP4, BMPR-IA, Eotaxin/CCL11, VEGF R1 (Flt-1), PDGF sR alpha, HCC-1/CCL14, CTLA-4, MCP-4/CCL13, GCP-2/CXCL6, TECK/CCL25, MDC/CCL22, Activin A, Eotaxin-2/MPIF-2/CCL24, Eotaxin-3/CCL-26 (aa 24-94), TRAIL R1 (DR4), VEGF R3 (Fit-4)/SDF-1 alpha(PBSF)/CXCL12, MSP, BMP-2, HVEM/VEGF R2 (KDR), Ephrin-A3, MIP-3 alpha/CCL20, MIP-3 beta/CCL19, Fractalkine/CX3CL1 (Chemokine Domain), TARC/CCL17, 6Ckine/CCL21, p75 Neurotrophin R (NGF R), SMDF, Neurturin, Leptin R/Fc Chimera, MIG/CXCL9, NAP-2/CXCL7, PARC/CCL18, Cardiotrophin-1 (CT-1), GFR alpha-2, BMP-5, IL-8/CXCL8 (Endothelial Cell Derived), Tie-1, Viral CMV UL146, VEGF-D, Angiopoietin-2, Inhibin A, TRANCE/RANK L, CD6/Fc Chimera, CF, dMIP-1 delta/LKN-1/CCL15 (68 aa), TRAIL R3/Fc Chimera, Soluble TNF R1, Activin RIA, EphAl, ENA-70, ENA-74, Eotaxin-3/CCL26, ALCAM, FGFR1 alpha (IIIc), Activin B, FGFT1 beta (IIIc), LIGHT, FGFR2 beta (IIIb), DNAM-1, Follistatin, GFR alpha-3, gp 130, I-TAC/CXCL11, IFN-gamma RI, IGFBP-2, IGFBP-3, Inhibin B, Prolactin CF, RANK, FGFR2 beta (IIIc), FGFR4, TrkB, GITR, MSP R, GITR Ligand, Lymphotactin/XCL1, FGFR2 alpha (IIIc), Activin AB, ICAM-3 (CD50), ICAM-1 (CD54), TNF RII, L-Selectin (CD62L, BLC/BCA-1/CXCL13, HCC-4/CCL16, ICAM-2 (CD102), IGFBP-4, Osteoprotegerin (OPG), UPAR, Activin RIB, VCAM-1 (CD106), CF, BMPR-II, IL-18 R, IL-12 R beta 1, Dtk, LBP, SDF-1 alpha (PBSF)/CXCL12 (synthetic), E-Selectin (CD62E), L-Selectin (CD62L), P-Selectin (CD62P), ICAM-1 (CD54), VCAM-1 (CD106), CD31 (PECAM-1), hedgehog family of proteins, Interleukin-10, Epidermal Growth Factor, Heregulin, HER4, Heparin Binding Epidermal Growth Factor, bFGF, MIP-18, MIP-2, MCP-1, MCP-5, NGF, NGF-B, leptin, Interferon A, Interferon A/D, Interferon B, Interferon Inducible Protein-10, Insulin Like Growth Factor-II, IGBFBP/IGF-1 Complex, C10, Cytokine Induced Neutrophil Chemoattractant 2, Cytokine Induced Neutrophil Chemoattractant 2B, Cytokine Induced Neutrophil Chemoattractant 1, Cytokine Responsive Gene-2, and any fragment thereof and their neutralizing antibodies. The dosage can be in the range of well-established effective concentrations; for example, dosage can be in the range of 0.1 to 5 times the maximum value of the $EC_{50}$, the concentration that provokes a response halfway between baseline and maximum.

Factors involved in cell-cell interactions that may be tested include but are not limited to the ADAM (A Disintegrin and Metalloproteinase) family of proteins including ADAM 1, 2, 3A, 3B, 4-31 and TS1-9, ADAMTSs (ADAMs with thrombospondin motifs), Reprolysins, metzincins, zincins, and zinc metalloproteinases and their neutralizing antibodies.

Adhesion molecules that may be tested include but are not limited to Ig superfamily CAM's, integrins, cadherins, including E-, P-, and N-cadherin, and selectins, and their neutralizing antibodies.

Nucleic acids that may be tested include but are not limited to those that encode or block by antisense, ribozyme activity, or RNA interference transcription factors that are involved in regulating gene expression during differentiation, genes for growth factors, cytokines, and extracellular matrix components, or other molecular activities that regulate differentiation.

Extracellular matrix component may also induce and direct the differentiation of stem cells. Members of the tenascin family are examples of extracellular matrix components that are useful in directing cell differentiation. There are currently five members of the family, tenascin-C (simply called tenascin in the examples below), and tenascins-R, -X, -Y and -W. Tenascin-R is especially useful in screens for agents that induce cells of the central nervous system, while tenascins-X and -Y are useful in screens relating to muscle cells. Tenascin-C is useful in differentiating a wide array of cell types, including neuronal and endodermal cells. Agents that block the action of the tenascins, such as neutralizing antibodies, and proteolytic subunits of the tenascins are also useful in directing differentiation. The tenascins or their subunits may be added to the culture substrate prior to the culture of the cells of interest, added to the media of the cultured cells, expressed by cells cocultured with the cells of interest, or otherwise introduced into contact with the cells.

Extracellular matrix components that may be tested include but are not limited to Tenascins, Keratin Sulphate Proteoglycan, Laminin, Merosin (laminin a2-chain), Chondroitin Sulphate A, SPARC, beta amyloid precursor protein, beta amyloid, presenilin 1,2, apolipoprotein E, thrombospondin-1,2, heparin, Heparan Sulphate, Heparan sulphate proteoglycan, Matrigel, Aggregan, Biglycan, Poly-L-Ornithine, the collagen family including but not limited to Collagen I-IV, Poly-D-Lysine, Ecistatin (viper venom), Flavoridin (viper venom), Kistrin (viper venom), Vitronectin, Superfibronectin, Fibronectin Adhesion-Promoting peptide, Fibronectin Fragment III-C, Fibronectin Fragment-30 KDA, Fibronectin-Like Polymer, Fibronectin Fragment 45 KDA, Fibronectin Fragment 70 KDA, Asialoganglioside-GM, Disialoganglioside-GOLA, Monosialo Ganglioside-$GM_1$, Monosialoganglioside-$GM_2$, Monosialoganglioside-$GM_3$, Methylcellulose, Keratin Sulphate Proteoglycam, Laminin and Chondroitin Sulphate A. Extracellular matrix components can be applied to the culture wells prior to or after adding the cells. When coating the well surfaces, the concentration of these components can be in the range of from 1 to 10 mg/ml, or from 0.2 to 50 mg/ml.

Media components that may be tested include but are not limited to glucose concentration, lipids, transferrin, B-Cyclodextrin, Prostaglandin $F_2$, Somatostatin, Thyrotropin Releasing Hormone, L-Thyroxine, 3,3,5-Triiodo-L-Thyronine, L-Ascorbic Acid, Fetuin, Heparin, 2-Mercaptoethanol, Horse Serum, DMSO, Chicken Serum, Goat Serum, Rabbit Serum, Human Serum, Pituitary Extract, Stromal Cell Factor, Conditioned Medium, Hybridoma Medium, d-Aldosterone, Dexamethasone, DHT, B-Estradiol, Glucagon, Insulin, Progesterone, Prostaglandin-$D_2$, Prostaglandin-$E_1$, Prostaglandin-$E_2$, Prostaglandin-$F_2$, Serum-Free Medium, Endothelial Cell Growth Supplement, Gene Therapy Medium, MDBK-GM Medium, QBSF-S1, Endothelial Medium, Keratinocyte Medium, Melanocyte Medium, Gly-His-Lys, soluble factors that inhibit or interfere with intracellular enzymes or other molecules including but not limited to compounds that alter chromatin modifying enzymes such as histone deacetylases such as butyrate or trichostatin A, compounds that modulates cAMP, protein kinanse inhibitors, compounds that alter intracellular calcium concentration, compounds that modulate phosphatidylinositol.

Environmental conditions that may be tested include but are not limited to oxygen tension, carbon dioxide tension, nitric oxide tension, temperature, pH, mechanical stress, altered culture substrates such as two vs. three dimensional substrates, growth on beads, inside cylinders, or porous substrates.

Materials derived from early stage embryos, fetuses, or adult tissues that may be tested include but are not limited to acellular extracellular matrix prepared by the detergent extraction of tissue from embryoid bodies, primitive endoderm, mesoderm, and ectoderm, and the anlagen of differentiating organs and tissues or living cells or tissues that when cocultured with the subject cells cause an induction of differentiation.

Growth factors, adhesion factors, extracellular matrix components, etc. may be tested individually or in various combinations. In addition, these factors may be combined with various culture conditions, e.g., vitamins and minerals, which may also have an affect on the differentiation of stem cells. For instance, it has been shown that oxygen tension may influence gene expression and development in embryoid bodies. Bichet et al., 1999, Oxygen tension modulates β-globin switching in embryoid bodies, FASEB J., 13: 285-95. In assay formats that expose test cells to a variety of different combinations, care should be taken to document the conditions applied to each sample so that results may be correlated to the appropriate test conditions.

Growth factors and other compounds may be applied to stem cells at about 0.1 to about 10 times their effective concentration; for example, at about 2 times their effective concentration, for varying periods of time, e.g. one hour to two months depending on the timing of differentiation of the cell of interest during normal development. Growth factors and other compounds can also be applied repetitively or in a particular temporal order with other compounds rather than simultaneously, with hours, days or weeks passing between different administrations.

Screening Assays:

An embodiment of the present invention uses a screening assay to identify agents or conditions that induce the differentiation of totipotent, nearly totipotent, or pluripotent stem cells, or cells therefrom; e.g., cells selected from the group consisting of embryonic stem cells, embryonic germ cells, embryoid bodies, ICM cells, formula-derived cells, non-ES stem cells, and cells therefrom, and to characterize the type and degree of differentiation that occurs in response to the agents or conditions tested. For example, a screening assay of the invention can comprise:

(a) separating individual totipotent, nearly totipotent, or pluripotent stem cells, or cells therefrom, or groups of individual cells, into one or a plurality of separate vessels which may be open or closed, which vessels may be in the same or different apparatus;

(b) isolating primary and/or progenitor cells from reference tissues and placing said primary and/or progenitor cells into separate vessels of a microarray thereby forming a control reference library;

(c) exposing said separate vessels of totipotent, nearly totipotent, or pluripotent stem cells, or cells therefrom, to the same one or more putative differentiation-inducing compounds either simultaneously or sequentially; and (d) comparing said individual totipotent, nearly totipotent, or pluripotent stem cells, or cells therefrom, or groups of cells, to said reference library in order to evaluate the differentiation of said individual cells or groups of cells.

High-Throughput Screening

A useful aspect of the present invention is that it provides means for screening a large number of different types of stem cells; e.g., a library of gene trap stem cells selected to have gene trap markers that are activated when the stem cells are induced to differentiate to a large number of different steps or "nodes" in the complex, branching tree of possible differentiation pathways leading to the partially or fully differentiated cell types of an animal. Moreover, the present invention also provides screening methods whereby one or more different types of stem cells are exposed to a large number of different types of chemical and biological agents and physical conditions, alone or in combination, simultaneously or in various temporal combinations, to identify sets of agents and conditions that induce the stem cells to partially or fully differentiate into cell types of interest.

In performing the assays of the invention disclosed herein, individual cells or individual groups of cells may be separated into any type of array apparatus or assembly of compartments that is convenient for systematically applying the test compounds and evaluating differentiation. For instance, the cells may be distributed into an apparatus comprising 10 to 100,000 different vessels or compartments, or for some embodiments 100 to 100,000 compartments, or for others 1000 to 10,000 compartments, or separate wells of one or more multi-well plates. The multi-well plates that are used can have any number of wells; for example, the screening assays of the invention can be performed using 24- or 96-well plates. In this embodiment, the reference library of primary cells may be freshly isolated and distributed in a similar array apparatus, or alternatively, frozen stock cells may be used. In distributing the cells into compartments, e.g., the wells of one or more 24- or 96-well plates, 1 to $10^6$ stem cells can be added per $cm^2$ of surface. For example, the screening assays of the invention can be performed by adding 10 to $10^5$ cells per $cm^2$ of surface. Some ES cells require a minimum number of cells to survive, for such cells, 3 to $10^6$ stem cells should be added per $cm^2$ of surface. Induction of differentiation by a given set of conditions occurs with a statistical probability; therefore, the more cells per well, the greater the likelihood that a cell in the cell will be induced to differentiate.

Reference Library Cells and Cell Type-Associated Markers

The primary and/or progenitor cells used for the reference library may include any cells of interest, i.e., any cells for which the operator is interested in identifying differentiation inducing compounds or compositions, including but not limited to brain cells, heart cells, liver cells, skin cells, pancreatic cells, blood cells, reproductive cells, nerve cells, sensory cells, vascular cells, skeletal cells, immune cells, lung cells, muscle cells, kidney cells, etc. The reference library cells are then used as an experimental control when testing the exposed stem cells for those that have differentiated into the particular primary cells in the reference library. Functional assays specifically geared toward detecting each of the cells in the reference library are performed on the treated or exposed stem cells to correlate differentiation with a particular cell type in the reference library.

For instance, depending on primary and secondary antibodies and other ligand reagents available and what is known about the molecular markers specific for particular cell types, immunocytochemistry may be used to test treated stem cells for the expression of proteins that correlate to specific cells in the library. Alternatively, RT-PCR may be used to test the samples for particular gene transcripts. There are many known molecular markers of differentiation of cell types that are detectable, e.g. with specific antibodies or by RT-PCR; examples include E-, P-, and N-cadherins, keratin, chAT, tyrosine hydroxylase, gamma enolase, PDX, amylase, CD34, VEGFR, cardiacmyosin, collagen II, sex determining region Y, frizzled-3, GATA 6, brachyury, PU.1 (Spi-1), hepatocyte nuclear factor-3, alpha-2 type XI collagen, hepatic lipase, nerve growth factor, sonic hedgehog, hematopoietically expressed homeobox, enolase-2, keratin 19, osteoblast-specific factor 2, globin transcription factor 1, myogenic factor 3, myosin heavy polypeptide 2, dopamine transporter, CD34, human serum albumin, pancreatin amylase, insulin promoter factor, beta-globin, Oct 4, cardiac alpha-myosin heavy chain, cardiac myosin light chain 1, fibroblast growth factor 5 (FGF-5), SOX-1, alpha-fetoprotein (AFP), EMX-2, engrailed-2 (En2), Hesx-1, Hox B1, Krox-20, Mush-1, Nkx-1, Nkx-2, Pax-3, Pax-6, nestin, and GAPDH (a housekeeping gene, useful as a control marker).

Cells in the reference library should be tested simultaneously as a positive control, to ensure that a negative result is not the failure of the assay itself rather than the absence of the particular protein or transcript. Functional assays could also be used to measure the production of enzymes or metabolites produced by the particular reference primary and/or progenitor cells, for instance by enzyme-linked immunosorbent assays (ELISA), high performance liquid chromatography (HPLC), Western blots, radioimmune assays, etc. For example, dopaminergic neurons could be tested for KCl induced dopamine release, β-cells for glucose dependent insulin release, cardiomyocytes for synchronous contraction, hepatocytes for triacylglycerol production, to name of few examples.

A second embodiment of the invention involves a method for evaluating the differentiation of totipotent, nearly totipotent, or pluripotent stem cells, or cells therefrom; in response to different compounds or combinations of compounds, comprising:
  (a) separating individual totipotent, nearly totipotent, or pluripotent stem cells, or cells therefrom, or groups of individual cells, into one or a plurality of separate vessels which may be open or closed, which vessels may be in the same or different apparatus;
  (b) systematically exposing said separate vessels of totipotent, nearly totipotent, or pluripotent stem cells, or cells therefrom, to a panel of different putative differentiation-inducing compounds or combinations thereof either simultaneously or sequentially; and
  (c) comparing said individual totipotent, nearly totipotent, or pluripotent stem cells, or cells therefrom, or groups of cells, to a reference differentiated or partially differentiated cell in order to evaluate the differentiation of said individual cells or groups of cells.

This embodiment differs from the first embodiment described above in that the cells are treated with a panel of different compounds and combinations of compounds, and the results are compared with a single reference control in order to identify particular conditions that resulted in directed differentiation into that cell type.

Although any of the functional assays described above may be used to analyze the results, this second embodiment is most amenable to the use of RNA expression profiles. For instance, expression profiles can be generated anytime at any pace and used to form a library that catalogs the RNA expression profiles according to what factors produced the specific profiles. Then, the profiles may be compared at any time to expression profiles from various reference primary cells in order to match each embryonic differentiation profile with a primary cell. Such libraries may be saved in electronic form, whereby matches in RNA expression profiles as between the library members and any particular primary or progenitor may be performed electronically rather than with the naked eye.

A third embodiment involves a method for evaluating the differentiation of totipotent, nearly totipotent, or pluripotent stem cells, or cells therefrom, in response to different compounds or combinations of compounds, comprising:
  (a) isolating a transfected totipotent, nearly totipotent, or pluripotent stem cell, or cell therefrom, wherein said cell is transfected with at least one reporter gene, the expression of which is operably linked to a promoter and/or gene of interest;
  (b) expanding said transfected cell in culture;
  (c) separating individual transfected cells or individual groups of transfected cells into one or a plurality of separate vessels which may be open or closed, which vessels may be in the same or different apparatus;
  (d) exposing said separate vessels of transfected cells to a panel of different putative differentiation-inducing compounds or combinations thereof either simultaneously or sequentially; and
  (e) analyzing said individual transfected cells or groups of cells in order to detect expression of said at least one reporter gene.

Alternatively, this embodiment may be performed using gene trap stem cells in which the marker DNAs are randomly inserted at sites such that they are expressed upon activation of genetic loci associated with the partial or complete differentiation of the stem cells to a particular cell type. Such cells serve as functional markers of differentiation, even when the genetic loci into which the markers are inserted have not been identified.

In this embodiment, transfected totipotent, nearly totipotent, or pluripotent stem cells, or cells therefrom, are exposed to a panel of different compounds and combinations of compounds, in order to identify those combinations that turn on expression of a particular reporter gene construct.

Stem cells comprising a relevant reporter gene constructs are known in the art as discussed supra, or alternatively, can be produced according to known methods. For example, a reporter gene may be targeted to the locus of a gene of interest, i.e., a gene specifically expressed in the cell or tissue type desired, by homologous recombination. By including an internal ribosome entry sequence (IRES) and designing the vector such that insertion occurs downstream of the endogenous stop codon, the transcript from the targeted locus will act as a bicistronic message, making both the endogenous protein and the protein encoded by the reporter gene. In this manner, the targeted gene will not be functionally disrupted. Alternatively, the targeted integration may be designed such that a fusion transcript, and/or fusion protein results.

A second approach would be to construct reporter transgenes using isolated promoter sequences for cell type specific genes. This approach is not as sophisticated since homologous recombination is not required, so it suffers from possible position variegation in transgene expression. However, the constructs may be made much more easily, and the use of good 5' and 3' flanking sequences, and possibly insulator sequences, could alleviate some of the variability.

The reporter gene strategy permits high-throughput and non-invasive screening. Specifically, cells could be continuously monitored, so the assay point would not be restricted to any particular time period during the differentiation process. The screening can be performed conducted by plating transgenic stem cells onto 96 well plates, for instance, and supplying each well with different conditions until reporter gene expression is detected. This would enable different styles of experimental design to rapidly be employed and evaluated. Further, this strategy could also be coupled to other functional and morphological markers in the same cell population.

Using the reporter gene strategy, the activation of gene expression specific to certain cells types may be quantified with respect to the purity of cells within the population. For example, the methods of the invention could include the further steps of:

(f) quantitatively determining the amount of detectable signal; and (g) comparing said amount of detectable signal with the amount of signal produced by the same number of said transfected cells in the absence of any test compound.

This aspect could also facilitate development of compound combinations that yield purer cell populations. In addition, cells expressing a reporter gene such as green fluorescence protein (GFP) may be purified from other cells or undifferentiated cells in the same sample by fluorescence activated cell sorting. Odorico et al., 2001, Multilineage differentiation from human embryonic stem cell lines, Stem Cells 19(3): 193-204.

Possible loci to be targeted for clinical applications are: insulin in β-cells, DOPA decarboxylase in dopaminergic neurons, cardiac α-actin in cardiomyocytes, and albumin in hepatocytes. Expression of these proteins are absolutely restricted to the corresponding cell types, thus should provide a reliable indicator or promoter source for the type of cells being produced.

Reporter Genes Useful as Markers:

Reporter genes useful for the present invention encode proteins that are detectable by any means, i.e., those that are detectable by the naked eye or after microscopic, photographic or radiographic analysis, or after contacting said exposed cells with a reagent selected from the group consisting of chromogenic substrates, dyes, sugars, antibodies, ligands, primers, etc. Suitable reporter genes may encode polypeptides including but not limited to green fluoresent protein (GFP), enhanced green fluoresent protein (EGFP), luciferase, chloramphenical acetyltransferase, β-glucuronidase, β-galactosidase, neomycin phosphotransferase, alkaline phosphatase, guanine xanthine phosphoribosyltransferase or β-lactamase. See, e.g., U.S. Pat. No. 5,928,88, herein incorporated by reference. The use of a marker gene encoding a fluorescent protein such as GFP permits detection of expression of the marker gene without injuring the cells. Fluorogenic substrates include but are not limited to fluorescein di-β-D-galactopyranoside, resorufin β-D-galactopyranoside, DDAO galactoside, methylumbelliferyl galactoside or its di-fluorinated analog, carboxyumbelliferyl galactoside, fuorescent glycolipids, Amplex Red Galactose, PFB Aminofluorescein, chloromethyl and lipophilic derivatives of DiFMUG, 4-methylumbelliferyl β-D-glucuronide, fluorescein di β-D-glucuronide, 5-(pentafluorobenzoylamino)fluorescein di β-D-glucuronide, DDAO β-D-glucuronide, etc. Those skilled in the art are familiar with many reagents for detecting glycosidase activity.

A fourth embodiment involves a method for evaluating the differentiation of transfected totipotent, nearly totipotent, or pluripotent stem cells, or cells therefrom, in response to one or more compounds, comprising:

(a) obtaining a library of transfected totipotent, nearly totipotent, or pluripotent stem cells, or cells therefrom, each transfected with at least one reporter gene, the expression of which is operably linked to a pre-characterized promoter and/or gene of interest;

(b) separating individual members of said library into one or a plurality of separate vessels which may be open or closed, which vessels may be in the same or different apparatus;

(c) exposing said separate vessels of transfected cells to the same one or more putative differentiation-inducing compounds either simultaneously or sequentially; and (d) analyzing said individual members of said library in order to detect expression of said at least one reporter gene.

This embodiment differs from the third embodiment described above in that a library of different transfected cells, each comprising a different reporter construct is exposed to a single test compound or test combination (rather than a panel of compounds being applied to a single type of stem cell representing a single reporter construct).

As for the previous embodiment, this embodiment may be performed using gene trap stem cells in which the marker DNAs are randomly inserted at sites such that they are expressed upon activation of genetic loci associated with the partial or complete differentiation of the stem cells to a particular cell type, as such gene trap cells function as markers of differentiation, even when the genetic loci in which they are is inserted are unidentified.

The present invention also includes identifying agents and/or conditions that induce stem cell differentiation, and then genetically modifying stem cells to facilitate isolation of a characterized population of the differentiated cells; e.g., to use in therapeutic trials in animal experimental models. A non-limiting example of how this can be done is to transfect the stem cells with a marker DNA encoding a non-immunogenic cell surface antigen that is inserted into a genetic locus that is specifically expressed in the differentiated cells to be isolated. Known methods, e.g., methods employing homologous recombination, can be used to target the marker DNA to the desired locus. When the genetically altered stem cells has differentiated into the desired cell type, the marker gene is expressed and the cells become tagged with the surface antigen. Methods for isolating genetically modified stem cells based on expression of a marker protein such as a surface antigen are described in Gay (U.S. Pat. No. 5,639,618), the contents of which are incorporated herein by reference. In an embodiment of this aspect of the invention, an isolation marker is inserted into a stem cell to be expressed when the cell has differentiated into a precursor of several specific cell types of interest. Additional isolation markers can be inserted into the same cell for expression when the precursor cells terminally differentiate into specific cell types. This permits isolation of either the precursor cells, or the terminally differentiated cell types. For example, an isolation marker could be inserted into the locus of the nestin gene, a marker of neural precursor cells, to permit isolation of neural precursor cells; and additional isolation markers can be inserted into genetic loci that are specifically expressed in neuronal cells, glial cells, and astrocytes, to permit efficient isolation of these cells types after induction of their differentiation from the neural precursor cells.

The present invention further includes identifying agents and/or conditions that induce stem cell differentiation, and then genetically modifying stem cells to constitutively express a marker gene that permits detection of differentiated cells derived from the genetically modified stem cells following their administration to an animal.

Accordingly, it is an embodiment of the invention to utilize cells from a species wherein a marker gene is used to identify a differentiated cell of interest, and to transfect these cells with a constitutively expressed marker such as Green Fluorescent Protein (GFP). Differentiated cells resulting from these embryonic cells are useful in testing the efficacy and safety of cell in cell therapy in animal or human models. Expression of the cell type-associated marker demonstrates to the investigator that the cell type of interest is present in the target tissue of interest, and the constitutively expressed marker identifies the administered cells against the background of the host cells of the animal into which the cells being tested were administered.

This embodiment may be performed by specifically preparing and characterizing a tailored panel of stem cells comprising a specific set of reporter constructs according to the techniques discussed above. Methods and materials for making and analyzing reporter gene constructs in eukaryotic cells, commonly called gene trap vectors, are known in the art and could be geared toward specific stem cells of interest once appropriate vectors are identified. See, e.g., U.S. Pat. No. 5,922,601, herein incorporated by reference in its entirety; see also Salminen et al., 1998, Dev. Dyn. 212(2): 326-33 and Stanford et al., 1998, Blood 92(12): 4622-31, each incorporated by reference in its entirety.

The members of any specially designed panel may be pre-characterized or specifically designed to be representative of a particular cell type or lineage. Procedures for preselecting and precharacterizing specific gene trap lines are known in the art. See Baker et al., 1997, Dev. Biol. 185(2); Thorey et al., 1998, Mol. Cell. Biol. 18(5): 3081-88; and Bonaldo et al., 1998, Exp. Cell Res. 244: 125-36, each of which is incorporated herein in their entirety. Alternatively, a panel of gene trap stem cells having random insertions may be accumulated, and the insertions that respond to a given compound or combination of compounds may be characterized subsequently to exposure and identification. For instance, the location of the insertion may be identified by molecular cloning following PCR of the flanking endogenous genetic material, and by sequencing outward from the inserted construct using well-established techniques. See, e.g., Gossler et al., 1989, Science 244(4903): 463-5, incorporated herein in its entirety.

A pluripotent cell that is particularly preferred for use in designing such a panel is the Cyno-1 cell line, a pluripotent primate stem cell line isolated from parthenogenetically activated oocytes from Cynomologous monkeys.

Screening with Pre-Existing ES Cell Gene Trap Libraries

In screening stem cells to determine agents and conditions that induce their differentiation to particular cell types, it is useful to use a gene trap stem cell library comprised of stem cells in which the marker genes are inserted in genetic loci that are normally activated when the cells is induced to differentiate, and are under transcriptional control of the endogenous promoters of the loci where they are inserted. This ensures that expression of the marker genes is controlled by the same regulatory signals (e.g., transcription factors and factors that alter chromatin structure) as the endogenous promoters of the loci where they are inserted.

As an alternative to preparing an entirely novel gene trap library, an embodiment of the present invention employs any of the murine ES cell gene trap libraries that are already known and available in the art. See, e.g., Cecconi & Meyer, 2000, FEBS Letts 480: 63-71; see also Durick et al., 1999, Genome Res. 9(11): 1019-25. For instance, the German Gene Trap Consortium (GGTC) has been established in Germany to provide a reference library of gene trap sequence tags (GTST) in mouse embryonic stem cells. See Wiles et al., 2000, Nature Genetics 24(1), incorporated by reference in its entirety. Sequence information on the GTST library is accessible at the Internet site of the GGTC, and the mutant ES cells are freely available upon request to the scientific community. Another library of gene trap murine ES cells, called OmniBank®, is also available from Lexicon Genetics, Inc. (The Woodlands, Tex.), who have reportedly characterized over 20,000 sequence-tagged mutations. The OmniBank® database may be searched using keywords or nucleotide or protein sequences via the Internet site of Lexicon Genetics, Inc. See also Zambrowicz & Friedrich, 1998, Int. J. Dev. Biol. 42(7): 1025-36; Zambrowicz et al., 1998, Nature 392: 609-11; see also U.S. Pat. Nos. 6,080,576, 6,207,371 and 6,136,566, each herein incorporated by reference in their entirety. Another group reported the successful recovery of 115 sequences from 153 cell lines using 5' RACE technology. Townley et al., 1997, Genome Res. 7: 293-298, incorporated by reference in its entirety. Sequence information from some of these murine ES cell clones is available on the University of California/Berkeley web site of the Skarnes lab. In addition, details on a large number of other academic mouse ES cell tagging efforts have also recently been reported. Chowdhury et al., 1997, Nucleic Acids Res. 25: 1531-1536; Hicks et al., 1997, Nat. Genet. 16: 338-344; Couldrey et al., 1998, Dev. Dyn. 212: 284-292; and Voss et al., 1998, Dev. Dyn. 212: 171-180, each of which is incorporated by reference herein in its entirety.

Gene-trap ES cells have been used to generate large numbers of mutant organisms for genetic analysis. The retrieval of transgenic mice made from gene trap ES cells has allowed for trapped genes to be characterized and segregated based on tissue expression profile, or subcellular expression characteristics. Some predict that genome-wide gene-trapping strategies, which integrate gene discovery and expression profiling, can be applied in a parallel format to produce living assays for drug discovery. Durick et al., 1999, supra. The use of gene trap clones in in vitro studies, on the other hand, has been limited.

U.S. Pat. No. 6,080,576 to Zambrowicz suggests using gene trap ES cells to screen for secreted molecules that induce apoptosis or hematopoietic cell differentiation. However, this approach is geared toward identifying insertions that cause over-expression of endogenous genes, and does not provide a format for systematically screening large numbers of compounds for their effect on stem cell differentiation. Similarly, Russ and colleagues disclose the identification of genes induced by factor deprivation in hematopoietic cells undergoing apoptosis using gene trap mutagenesis. Russ et al., 1996, Identification of genes induced by factor deprivation in hematopoietic cells undergoing apoptosis using gene-trap mutagenesis and site-specific recombination, Proc. Natl. Acad. Sci. USA 93: 15279-84. However, this approach looks for genes activated during programmed cell death rather than genes activated during embryonic or stem cell differentiation.

Era and colleagues utilize a LacZ reporter gene similar to that used in gene trap strategies in order to characterize hematopoietic lineage-specific gene expression by ES cells in an in vitro differentiation induction system. Era et al., 2000, Blood 95(3): 870-78. However, this approach was geared toward analyzing a particular promoter of interest and determining which section of the promoter was responsible for differentiation-induced expression. There was no suggestion to use the promoter constructs to screen for growth factors or other compounds that are involved in particular cell lineage differentiation pathways.

Bonaldo and colleagues used gene-trap and pre-selection analysis of isolated cell lines to identify fusions that are expressed during embryonic development in response to specific, single growth factors. They do not use the cells identified, however, to screen for combinations of factors that direct the development of those cells. In fact, the low-serum medium employed in the screening process was only suitable for short term screening lasting about 24 hours. See Bonaldo et al., 1998, supra. Thus, Bonaldo et al. presents a means of preselecting and precharacterizing cells containing fusions in the early developing embryo, but does not disclose the use of such cells in screening for factors that direct the differentiation of specific cells and tissues.

Similarly, Forrester and colleagues used gene-trap technology to identify genes specifically expressed in response to retinoic acid during embryogenesis. Forrester et al., 1996, An induction gene trap screen in embryonic stem cells: Identification of genes that respond to retinoic acid in vitro, Proc. Natl. Acad. Sci USA 93: 1677-82. However, they also did not use such cells to screen for growth factor combinations that direct the development of specific cells and tissues.

Thus, this is the first disclosure of which the present inventors are aware, that proposes to use the gene trap ES cell libraries as a tool for screening growth factors, adhesion factors, extracellular matrix materials, etc., for compounds and combinations that mediate the directed differentiation of stem cells. The ES cells identified as corresponding to a specific combination of growth factors may be used to make transgenic embryos or animals, in order to correlate in vivo temporal and spatial gene expression with the in vitro data obtained in the disclosed method.

As indicated by the foregoing description, libraries of totipotent murine and non-human gene trap stem cells can be assembled from existing cell lines, or novel libraries can be made using known techniques. When gene trap marker DNAs are inserted randomly, developing or mature animals cloned from the gene trap ES cells can be sacrificed and analyzed histologically to identify the gene trap stem cell lines that contain markers that are activated in particular cell types for use in the screening assays of the invention.

Alternatively, gene trap marker DNAs can be inserted into ES or EG cells, either directly or by deriving genetically modified ES or EG cells from a nuclear transfer embryo produced with a genetically modified nuclear donor cell. For example, a library of totipotent human gene trap stem cells can be produced by deriving a set of genetically modified human ES or EG cells from nuclear transfer embryos produced with genetically modified nuclear donor cells. The gene trap ES or EG cells are then expanded and used to produce embryoids containing diverse types of differentiated cells. Histological analysis is performed to identify the gene trap stem cell lines that contain markers that are activated in particular cell types for use in the screening assays of the invention. Alternatively, the totipotent cells can be injected into an animal to produce teratomas containing diverse types of differentiated cells, and histological analysis of these performed to identify the gene trap stem cell lines that contain useful markers of differentiation.

The present invention has broad applications. For example, in addition to identifying agents and conditions that induce and direct differentiation, the screening methods of the present application permit identification of agents and conditions that promote cell survival (survival factors), and of agents and conditions that promote mitogenesis (mitogenic factors). For example, cells are cultured for a period of 1-14 days with exposure to a panel of different agents and conditions that are putative survival and/or mitogenic factors, and the effects of the various treatments on cell survival and/or cell proliferation over the time interval of the assay is determined. Agents and conditions that decrease the loss or death of particular cell types can be detected by the assay in this manner, and may be regarded as survival factors. Similarly, agents and conditions that increase cell proliferation over the course of the assay are mitogenic factors. The combination of information regarding differentiation, survival, and mitogenic factors is useful in identifying and optimizing conditions that are useful for producing desired quantities of medically useful cell types.

In another aspect, the invention encompasses compositions and formulations comprising the compounds and compositions identified using the disclosed methods, and the use thereof to direct the development of cells and tissues from totipotent, nearly totipotent, and pluripotent stem cells, and cells therefrom, to isolate cells and tissues for use in treatments and transplantation therapies. In particular, the identified combinations of factors may be used to induce the differentiation of cells on polymeric matrices, i.e., as disclosed in U.S. Pat. Nos. 6,214,369, 6,197,575, and 6,123,727, each of which is herein incorporated by reference in its entirety.

The combinations identified by the disclosed methods may also be used to induce the production of different types of cells, either separately or in conjunction, in order to design and recover tissues and/or artificial organs constituted of different cell types.

Other embodiments, variations and modifications of the assays and methods disclosed herein will be envisioned by those in the art upon reading the present disclosure, and should also be included as part of the invention.

Example 1

Conditioning Totipotent Stem Cells to Grow and Maintain an Undifferentiated State in the Absence of Feeder Cells:

ES-like cells derived from the inner cell mass of parthenogenetic Cynomologous monkey embryos, Cyno-1 were originally cultured on mitotically inactivated mouse embryonic fibroblast derived from D12 fetuses (strain 129).

The culture media was:

| | |
|---|---|
| DMEM (High Glucose) (Gibco # 11960-044) | 425 ml |
| Fetal Calf Serum (Hyclone) | 75 ml |
| MEM non essential AA x100 (Gibco #11140-050) | 5 ml |
| L-Glutamine | 4 mM |
| 2-mercatoethanol (Gibco #21985-023) | 1.4 ml |

The cells were passaged mechanically every 4 to 5 days.

To condition the cells to grow in the absence of feeder cells to improve the screening assay, the cells were passaged mechanically into a non-coated Polystyrene cell culture plate (Corning)

For the first two days, cells were cultured in conditioned media from the original cultures (described above)

On day three, conditioned media was replaced by:

Human Endothelial-SFM Basal Growth Medium (Gibco #11111-044) 500 ml

EGF-Human Recombinant (Gibco #10458-016) 10 μg bFGF (Gibco #13256-029) 10 μg

Human Plasma Fibronectin (Gibco #33016-023) 1 mg

The colonies maintained their pluripotent phenotype (morphology and AP staining) for up to one week. The cultures appeared that grew in the absence of feeder fibroblasts while maintaining an undifferentiated state. This new line designated Cyno-1FF displays the morphology of undifferentiated ES-like cells in that they have small cytoplasmic to nuclear ratios, prominent nucleoli, and are alkaline phosphatase positive (FIG. 1).

Example 2

Screen Using Primate ES-Like Cells and Analysis by Microscopy and RT-PCR:

Approximately $10^5$ ES-like stem cells from parthenogenetic monkey embryos (Cyno-1FF cell line, see Example 1) were plated in duplicate 24 well plates in the presence of mouse embryonic fibroblast-conditioned medium for two days. The media was then aspirated and replaced with DMEM medium with 15% fetal bovine serum, added nonessential amino acids, $5\times10^{-5}$ M β-mercaptoethanol, 2 mM L-glutamine, 100 µg/ml penicillin, and 100 µg/ml streptomycin. The cells were then cultured in the presence of growth factors or cytokines in order to direct their differentiation. Working stock solutions of the cytokines were prepared in 0.1% bovine serum albumin (BSA) in phosphate-buffered saline (PBS). Diluted cytokines were applied on Day 0. To each well, 7.5 µl of diluted factor was added from the working stock solutions to obtain the following final concentrations:

VEGF-A (165 kDa) (R&D Biosystems cat #293VE) was used at 20 ng/mL,
LAP (R&D #246-LP) at 50 ng/mL,
Flt-3/Flk-2 ligand (R&D #308-FK) at 5 ng/mL,
TGF beta-1 (R&D #240-B) at 0.1 ng/mL,
IGF-1 (R&D #291-G1) at 10 ng/mL,
PlGF (R&D #264-PG) at 20 ng/mL,
Tie-1/Fc chimera (R&D #619-TI) at 100 ng/mL,
BMP-2 (R&D #355-BM) at 500 ng/mL,
BMP-4 (R&D #314-BP) at 250 ng/mL,
BMP-5 (R&D #615-BM) at 2 µg/mL,
FGF-17 (R&D #319-FG) at 50 ng/mL,
TGF-alpha (R&D #239-A) at 0.5 ng/mL,
Fibronectin (human 120 chymotryptic fragment, Gibco #12159-018) at 50 ng/mL,
Merosin (Gibco #12162-012) at 50 ng/mL,
Tenascin (Gibco #12175-014) at 50 ng/ml,
IL-1-alpha (R&D #200-LA) at 10 µg/mL,
FGF-4 (R&D #235-F4) at 0.25 ng/mL,
SCF (R&D #255-SC) at 10 ng/mL,
bFGF (R&D #233-FB) at 1.0 ng/mL,
PDGF (R&D #120-HD) at 5.0 ng/mL,
PECAM-1 (R&D #ADP6) at 1.0 µg/mL,
anti-FGF-4 antibody (R&D #AF235) at 0.5 µg/mL,
anti-Cripto-1 antibody (R&D #AF145) at 0.5 µg/mL,
and a control of the same volume of 0.1% BSA in PBS.

To coat a well with an ECM component, a solution of the ECM component at a concentration of 10 µg/mL in PBS was added to the well to be coated and incubated for at least one hour, and then removed by aspiration.

The plates were cultured at 37 deg. C. at atmospheric $O_2$ and 5% $CO_2$, one for three and one for ten days. Table 1 in FIG. 2 identifies the factors that were added to each of the wells of duplicate 24-well plates. One plate was harvested on Day 3, and the other plate was harvested on Day 10. Analysis by phase contrast microscopy and RT-PCR revealed many unique differentiated cell types, as discussed below.

Figure 3:
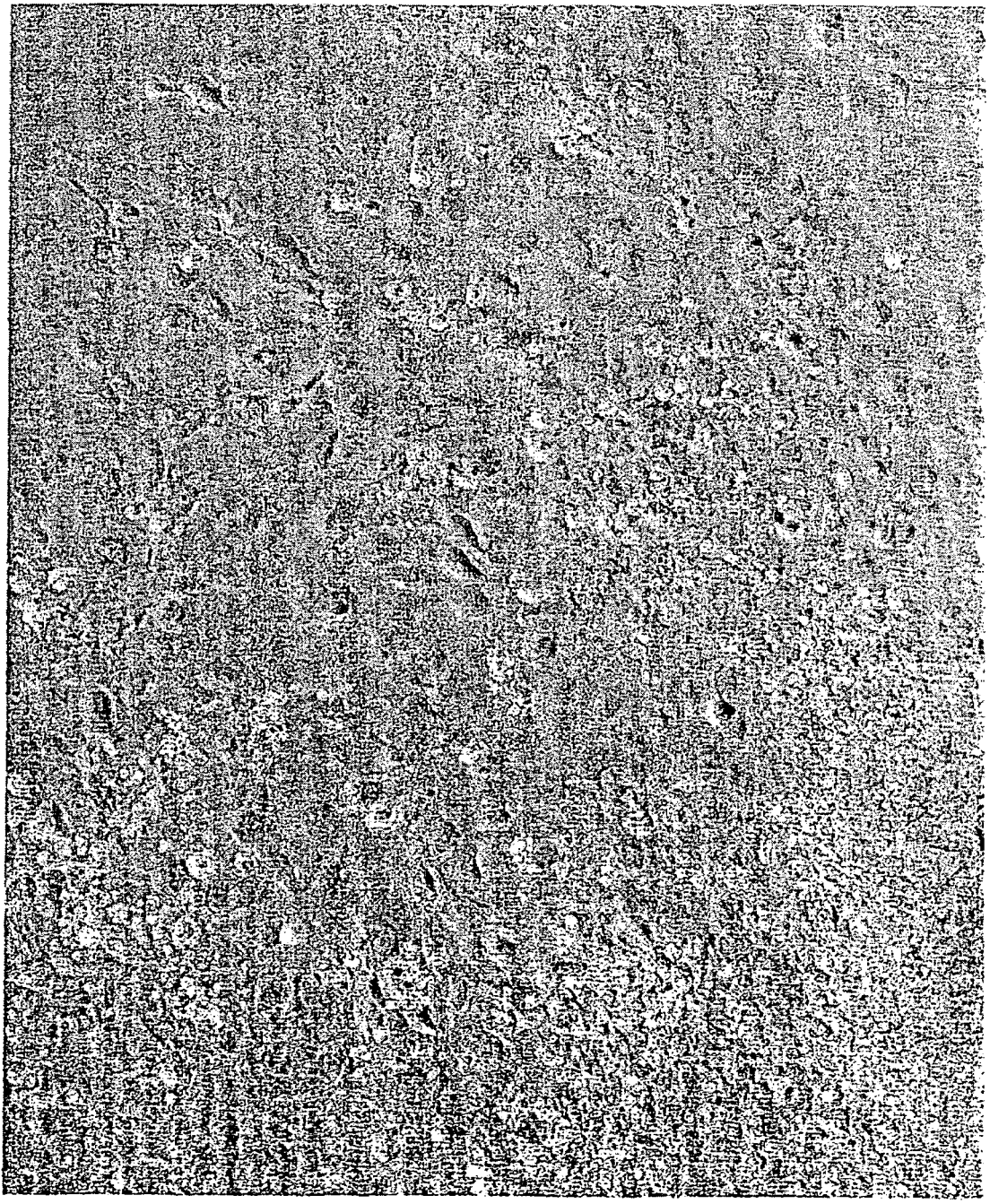
FIG. 3 is a photograph showing Cyno-1FF cells that were exposed to Flt-3 ligand.

Analysis of Cell Morphologies by Phase Contrast Microscopy:

Following exposure to Flt-3 ligand, the Cyno-1FF ES-like cells differentiated into cells that appeared to be vascular endothelial cells (derivatives of mesodermal differentiation). Cells having the appearance of vascular endothelial cells were observed by five days in the wells with added Flt-3 ligand, and were more evident in these wells by day 11. FIG. 3 is a photograph of primate Cyno-1FF cells exposed to Flt-3 ligand.

Figure 4:
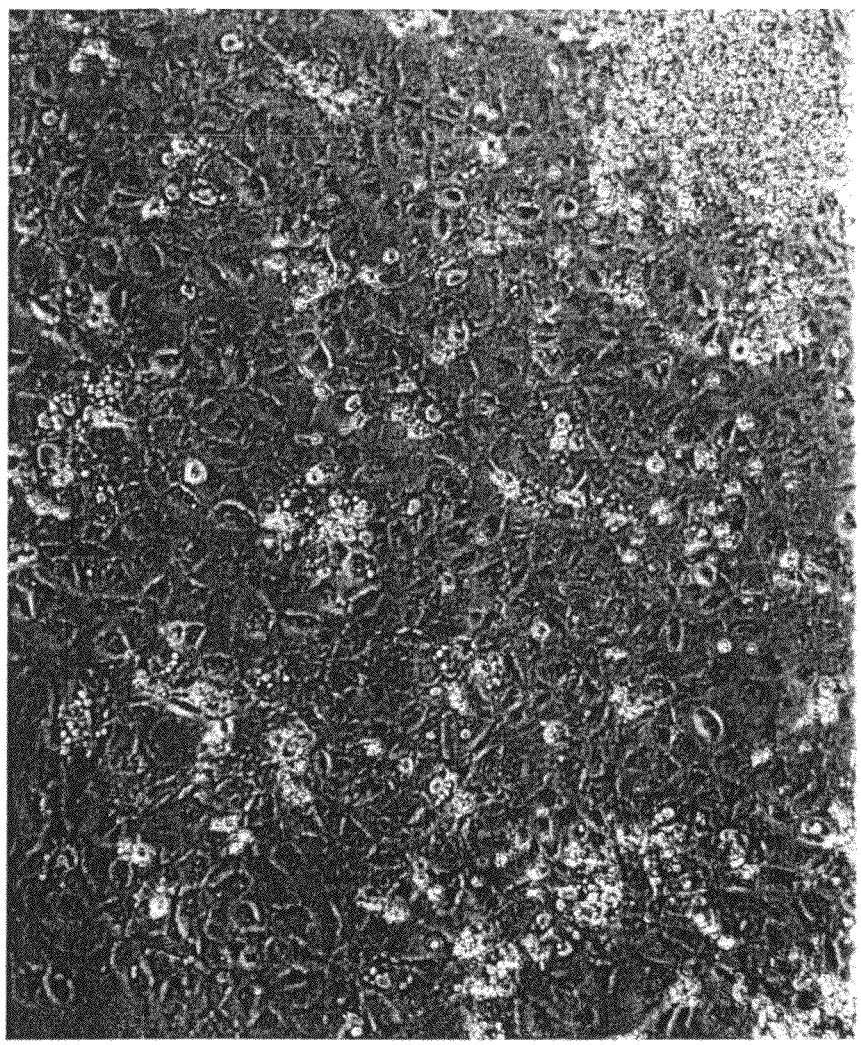
FIG. 4 shows mesoderm and cells with the morphology of nestin positive neuronal stem cells obtained by culturing Cyno-1FF cells in the presence of TGF beta-1.

Exposed to TGF beta-1 induced Cyno-1FF cells to acquire morphologies that appeared to be those of mesodermal and neural stem cells. FIG. 4 shows mesoderm and cells with the morphology of nestin positive neuronal stem cells obtained by the culture of Cyno-1FF cells in the presence of TGF beta-1.

Figure 5:
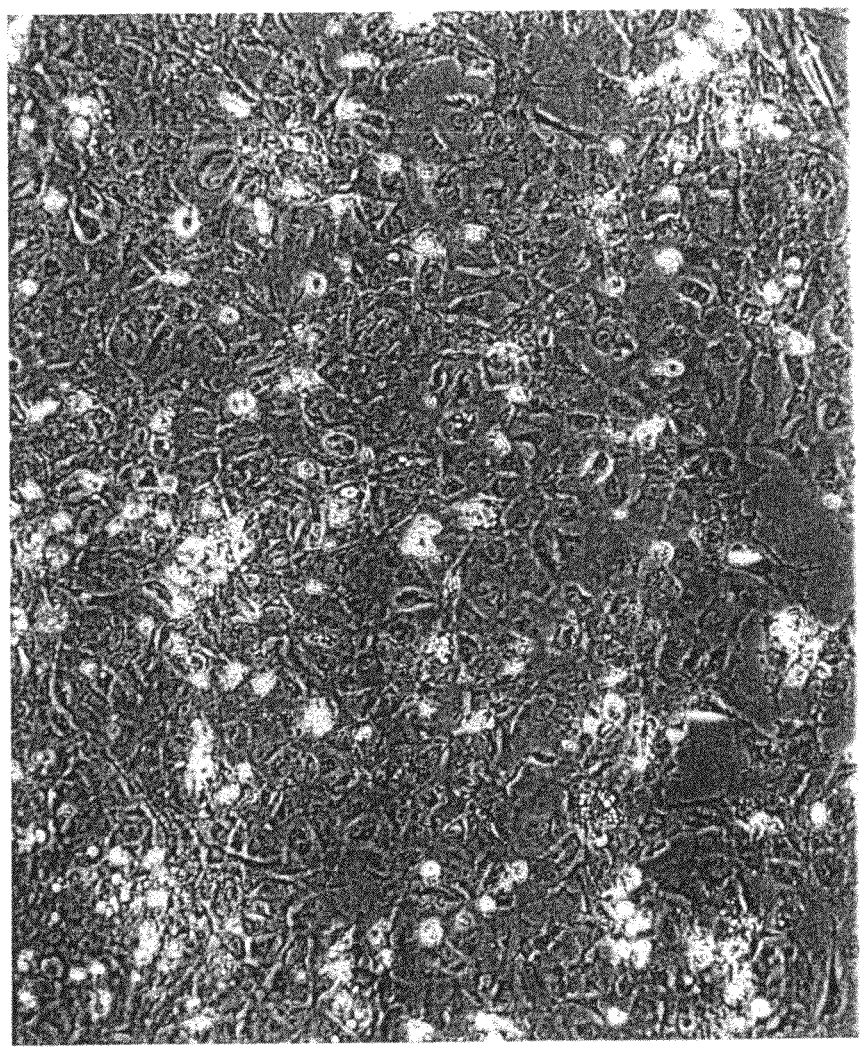
FIG. 5 shows cells having the appearance of endodermal precursor cells obtained by culturing Cyno-1FF cells in the presence of the extracellular matrix protein tenascin.

Cyno-1FF cells cultured in the presence of the extracellular matrix protein tenascin induced the formation of a distinctive population of cells that had the appearance of endodermal precursor cells. The appearance of the cells in the presence of tenascin was strikingly different from that of the cells in the control well. This result indicates that different concentrations of this particular extracellular matrix component and/or its removal or inactivation can be used to direct the differentiation of totipotent and pluripotent stem cells. FIG. 5 shows cells with the appearance of endodermal precursor cells obtained by the culture of Cyno-1FF cells in the presence of the extracellular matrix protein tenascin.

Figure 6:
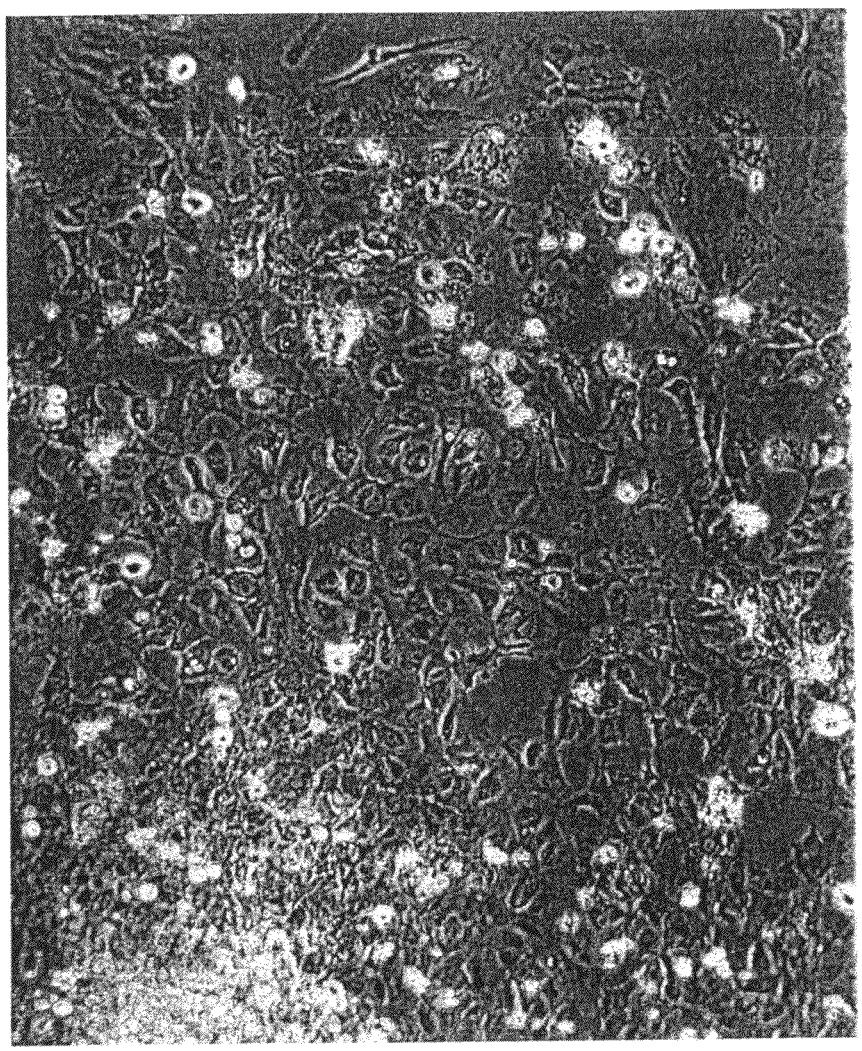
FIG. 6 shows Cyno-1FF cells exposed to a chimeric protein made from the receptor for Tie-1 and an immunoglobulin Fc region.
Figure 7:
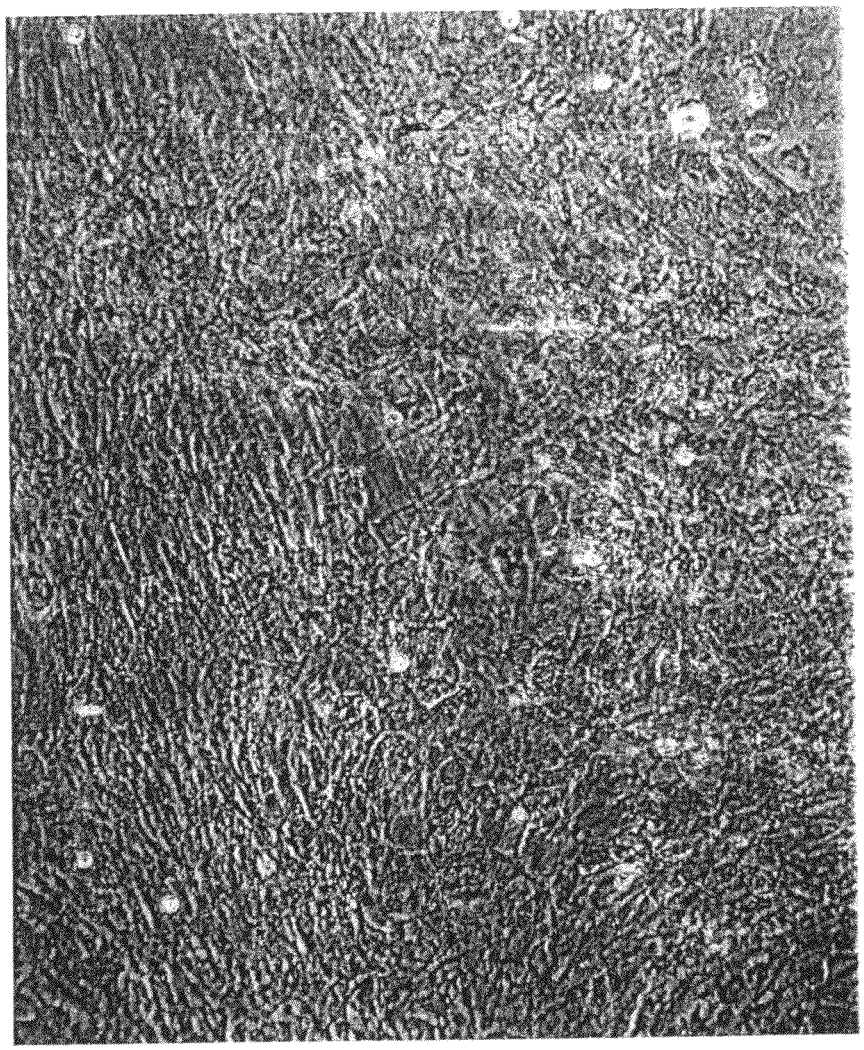
FIG. 7 shows fibroblast-like connective tissue cells produced by culturing Cyno-1FF cells in the presence of BMP-2.

Cyno-1FF cells that were exposed to other putative differentiation-inducing agents in other wells of the assay plate were also induced to differentiate to have distinctive morphologies and to express cell type-associated genes. For example, FIG. 6 shows the appearance of cells cultured in the presence of Tie-1 receptor/Fc chimera. Cells cultured in the presence of BMP-2 acquired the morphology and appearance of connective tissue fibroblast-like cells, as shown in FIG. 7.

RT-PCR Analysis of Expression of Cell Type-Associated Genes:

The expression of cell type-associated genes by the Cyno-1FF cells exposed to the panel of putative differentiation-inducing agents shown in FIG. 2 was assayed by RT-PCR using the following standard protocols.

(a) RNA was harvested from cells using kit: Ultraspec-II RNA, Item No. BL-12050 (Bioflex Labs, Inc) and included protocol.

(b) The isolated RNA was amplified using listed primers and kit: Enhanced Avian RT First Strand Synthesis kit, Item No. STR-1 (Sigma-Aldrich, Inc)

(c) The amplified RNA was harvested from cells and stored at −70° C. in ethanol.

(d) Reverse transcription reaction:
RNA was resuspended to 30 ul, and the following reagents were added:
2 ul dNTP mixture
2 ul Random nonamers
the mixture was heated to 80° C. for 12 minutes, then transferred to an ice bath for 5 minutes
the following reagents were added:
4 ul 10×RT buffer
1 ul RNAse inhibitor
2 ul reverse transcriptase
the reaction was then thermocycled using the following conditions:

24° - 15 min
42° - 50 min
95° - 30 sec
4° - hold the mixture was then aliquotted with 3 ul/sample and was stored at −70° C. until use.

(e) Polymerase chain reaction:

The following reagents were added to each sample:

2 ul primer pair mix (50 pmol/ul)

5 ul MgCl2

PCR reaction mixture (for each sample):

5 ul 10× buffer (without Mg)

4 ul dNTP mix (10 mM)

0.5 ul Taq (Sigma)

0.055 ul HotStart Taq (Qiagen)

30.5 ul H2O the reaction was then thermocycled for 35 cycles using the following conditions:

```
94° C. - 2 min
94° C. - 30 sec
45° C. - 1 min
72° C. - 2 min
72° C. - 10 min
 4° C. - hold
```

The primers that were used to detect expression of cell type-associated genes by RT-PCR, and the expected sizes of the products, are shown in Table 2 shown in FIG. 8. The PCR products were visualized by polyacrylamide gel electrophoresis, ethidium bromide staining, and illumination with uv light. The bands were identified by predicted size and relative intensity determined by comparison with GAPDH intensity.

Figure 9:
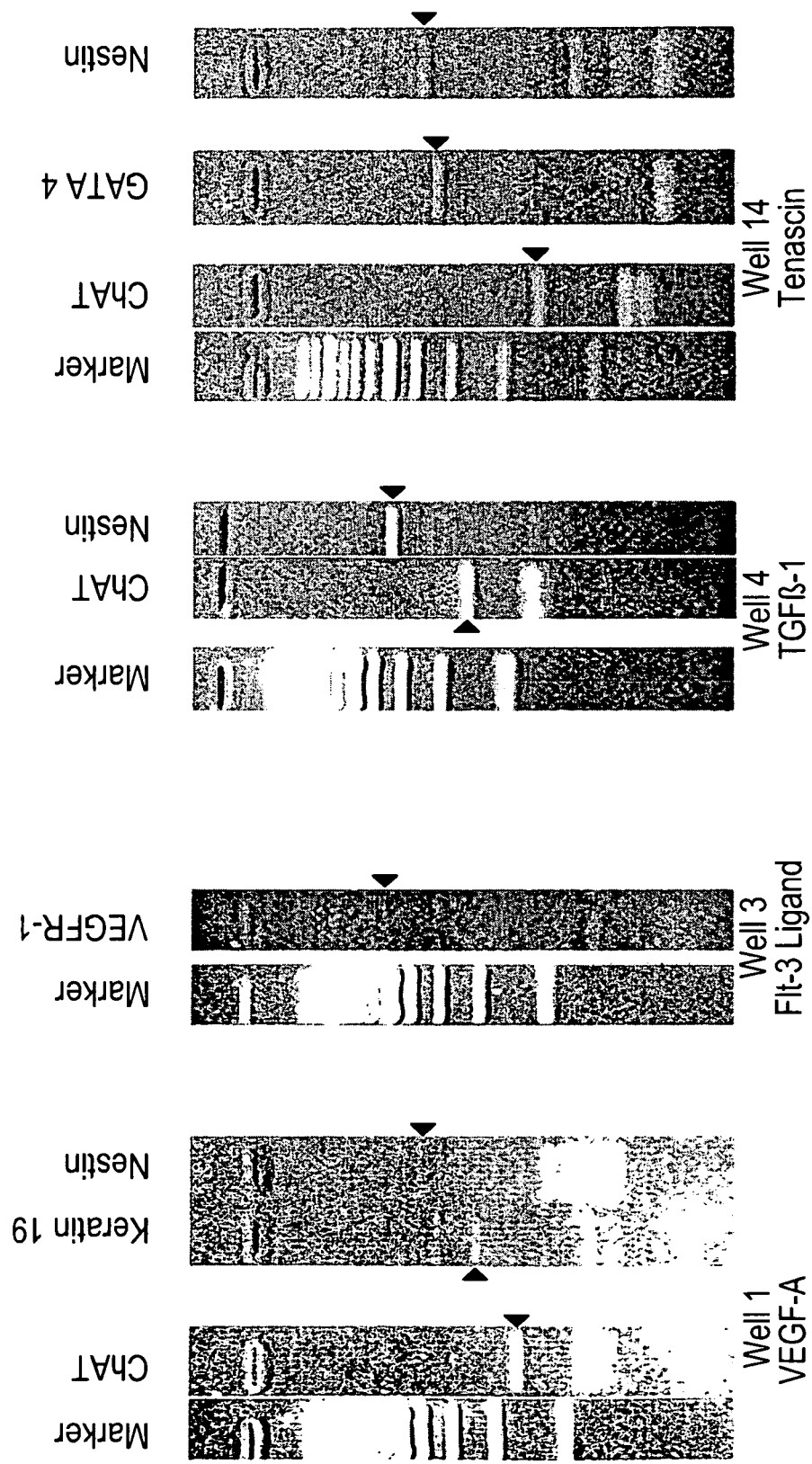
FIG. 9 shows examples of the results of RT-PCR analysis of cells from four different wells, each containing a different inducing agent (see Example 2). The figure shows photographs of the lanes of electrophoretic gels in which the DNA molecules produced by RT-PCR were separated, stained with ethidium bromide, and illuminated with uv light.

Examples of the results, demonstrating detection of specific differentiation pathways in the endoderm, mesoderm, and ectoderm germ layers in the wells by RT-PCR, is shown in FIG. 9.

FIG. 9 shows that Cyno-1FF cells induced to differentiate by different differentiation-inducing agents express different but sometimes overlapping combinations of cell type-associated genes. For example, cells exposed to VEGF-A expressed ChAT, keratin-19, and nestin, and cells exposed to tenascin expressed ChAT, nestin, and GATA-4. The strongest induction of ChAT (choline acetyltransferase) and therefore, of neuronal differentiation was seen in well 10-14 in the presence of the extracellular matrix component tenascin, and in well 10-15 in the presence BMP-5. ChAT was also induced by TGF-beta-1, IGF-1, FGF-4, bFGF, tenascin, and anti-Cripto-1 antibody. The best endothelial/hematopoietic conditions observed were in the presence of Flt-3 ligand. This correlated well with the endothelial morphology observed by phase contrast shown in FIG. 3. Interestingly, the best conditions observed to induce endothelial differentiation were also in the presence of the extracellular matrix component tenascin.

In contrast to the results obtained with cells cultured in wells containing differentiation-inducing agents as described above, expression of cell type-associated genes by control Cyno-1FF cells cultured in medium without the added putative differentiation-inducing agents was no detected by the RT-PCR assay. This result is evidence that the above-described assay detected genuine differentiation-inducing effects.

Example 3

Screen Using Primate ES-Like Cells and Analysis by Immunocytochemistry:

The presence of products of the expression of cell type-associated genes in Cyno-1FF cells exposed to putative differentiation-inducing agents in one of the 24 well plates prepared according to Example 2 was detected by immunocytochemistry (ICC).

Solutions for Immunocytochemistry:

Fixative: 4% Paraformaldehyde

Permeabilization Solution: DPBS+1% TritonX-100

Blocking Solution: DPBS+150 mM glycine+3 mg/ml BSA

Rinsing Solution: DPBS+0.1% Triton X-100

Antibody Diluent: DPBS+0.1% Triton X-100+3 mg/ml BSA

General Protocol for Immunocytochemistry:

Rinse cells in DPBS (with Ca/Mg so cells do not dissociate) 3×.

Add 4% Paraformaldehyde, Incubate at RT for 20-30 min.

Remove fixative with a Pasteur pipette and wash 3× with PBS. At this point cells can be stored at 4 C for long periods of time if wrapped in parafilm.

Add blocking solution and incubate at RT for at least 1 hour (this can be prolonged as long as overnight).

Remove blocking solution and replace with primary antibody (diluted . . . generally dilutions of 1:10 to 1:100 work well).

Incubate at RT for at least 1 hour.

Remove primary antibody and wash 3× with PBS over 45 minutes.

Add secondary antibody (diluted . . . generally dilutions of 1:50 to 1:500 work well).

Rinse 3× in PBS over 45 minutes. Add 5 ug/ml Hoechst or DAPI to first rinse.

Sample is ready for imaging.

Antibodies Used:

GATA4: Item # sc-1237 (Santa Cruz Biotechnology, Inc.)

Goat IgG used at dilution of 1:75

Nestin: Item #611659 (BD Transduction Laboratories, Inc)

Mouse IgG1 used at dilution of 1:75

Desmin: Item #D-1033 (Sigma-Aldrich, Inc)

Mouse IgG1 used at dilution of 1:20

Goat anti-Mouse IgG-FITC conjugate: Item #F-0257 (Sigma-Aldrich, Inc)

Used at dilution of 1:50

Mouse anti-oat IgG-FITC conjugate: Item #sc-2356 (Santa Cruz Biotechnology, Inc.)

Used at dilution of 1:50

Figure 10:
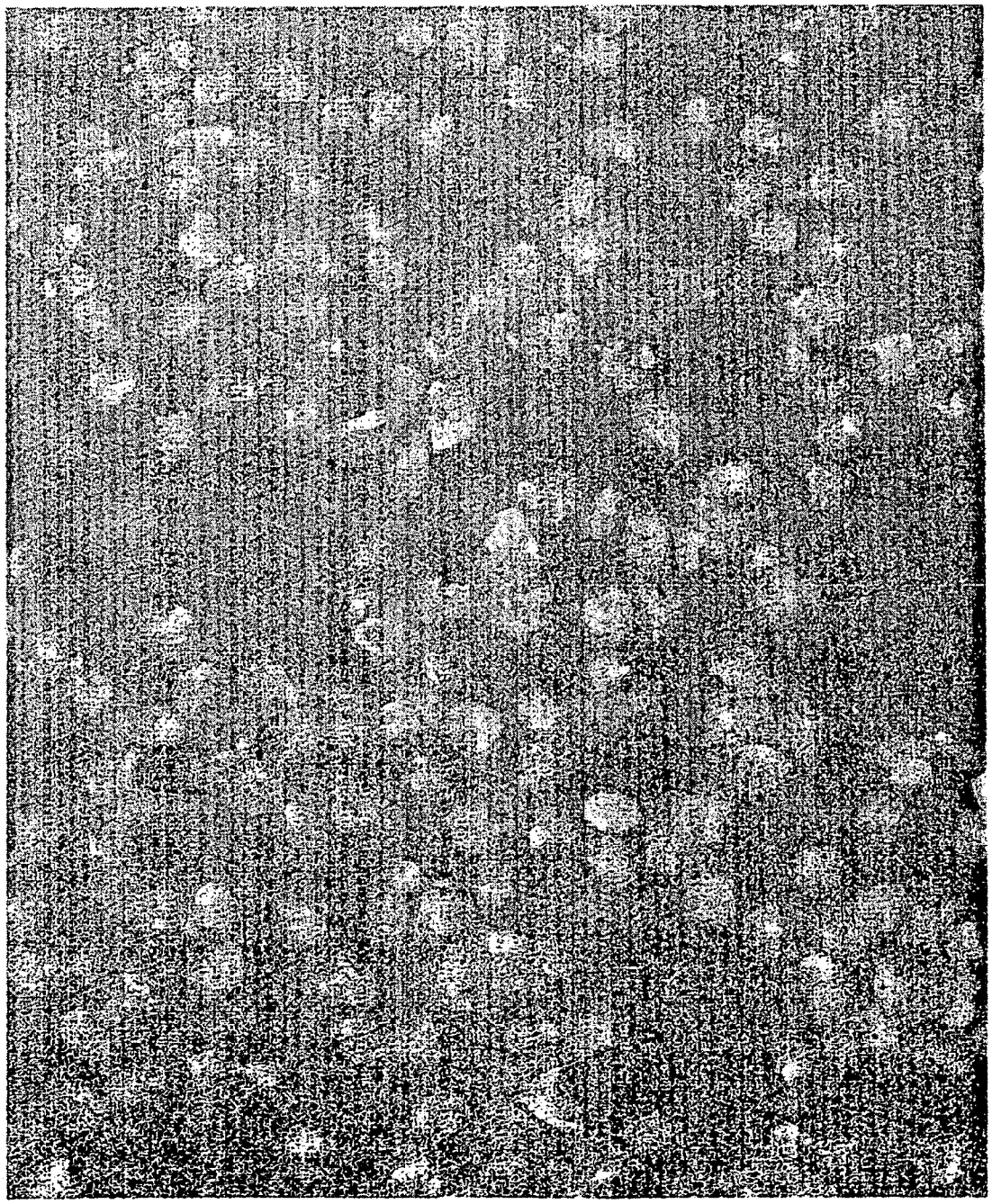
FIG. 10 shows the detection of desmin by ICC in Cyno-1FF cells exposed to a differentiation-inducing agent (see Example 3).
Figure 11:
FIG. 11 shows the detection of nestin by ICC in Cyno-1FF cells exposed to a differentiation-inducing agent (see Example 3).

The ICC assay successfully detected gene expression products associated with each of the three embryonic germ layers. FIG. 10 demonstrates the detection by ICC of desmin, a marker for mesoderm, and FIG. 11 demonstrates the detection of nestin, primarily a marker for ectoderm, but sometimes of endoderm, in Cyno-1FF cells exposed to differentiation-inducing agents. The expression of GATA4, a marker for endoderm, was also detected by ICC in Cyno-1FF cells exposed to differentiation-inducing agents (results not shown).

Example 4

Screen Using Primate ES Cells, Induction of Differentiation by Physical Conditions:

Cyno-1FF ES-like cells were plated in wells of a 24 well plate as described in Example 2, and were incubated under low oxygen partial pressure (5%). A control plate of the same cells was incubated in ambient oxygen. Analysis of cellular morphologies showed that the cells incubated under low oxygen partial pressure (5%) were induced to acquire different morphologies than the control cells incubated under ambient oxygen. This example demonstrates the importance of screening various physical as well as chemical factors to identify conditions or factors that induce differentiation of stem cells into desired cell types.

Example 5

Figure 12:
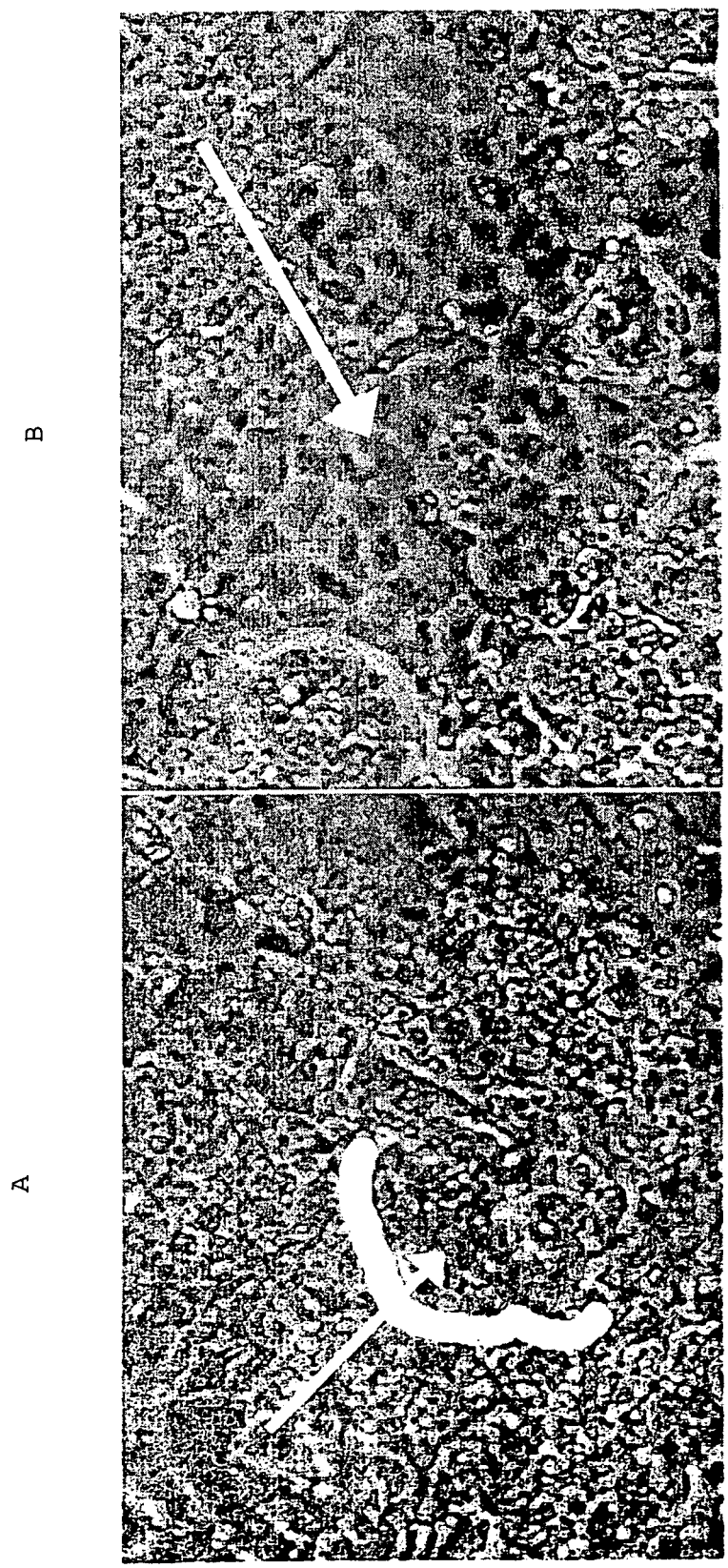
FIGS. 12A and 12B are phase contrast photographs of the cells in well #16 of Example 5 that were exposed to IL-1-alpha.

Screen for Agents that Induce Differentiation of Murine ES Cells into Myocardial Cells:

Approximately 20,000 murine ES cells (strain J1) were plated in a 24 well tissue culture plate without feeder fibroblasts or LIF in 1.5 mL of DMEM Medium with 15% fetal bovine serum, added nonessential amino acids, $5 \times 10^{-5}$ M 2-mercaptoethanol, 2 mm L-glutamine, 100 ug/ml penicillin, and 100 ug/ml streptomycin. The cells were incubated and allowed to differentiate in the presence of the same added factors and in the same manner as described in Example 2. After ten days of differentiation, the morphologies of the cells were examined by phase contrast microscopy to detect rhythmically contracting cells as evidence of myocardial differentiation. Only one well, well #16 containing IL-1-alpha, contained contracting rhythmically myocardial cells. Interestingly, these cells were and consistently found to be growing in association with underlying endothelial cells. FIGS. 12A and 12B are phase contrast photographs of the cells in well #16. The arrowhead in the figure on the left (FIG. 12A) points to a beating myocardial cell. The arrowhead in the figure on the right (FIG. 12B) points to an endothelial cell inducers adjacent to myocardial cells.

Example 6

Screen for Agents that Induce Differentiation of Murine ES Cells; Detection by ICC:

Approximately 5,000 murine ES cells (strain J1) were plated in a 24 well tissue culture plate without LIF in 1.5 mL of DMEM Medium with 15% fetal bovine serum, added nonessential amino acids, $5 \times 10^{-5}$ M 2-mercaptoethanol, 2 mM L-glutamine, 100 ug/ml penicillin, and 100 ug/ml streptomycin. The cells were allowed to differentiate in the presence of FGF4 and/or TGF-beta-1 (concentrations as in Example 2), in the presence or absence of inducer fibroblasts, or in the presence or absence of type I collagen and human plasma fibronectin (the wells were precoated by incubating for an hour with 10 ug/mL of the ECM proteins, and then removing and rinsing in PBS). The combinations of putative differentiation-inducing agents in each well are shown in Table 3 of FIG. 13.

Figure 14:
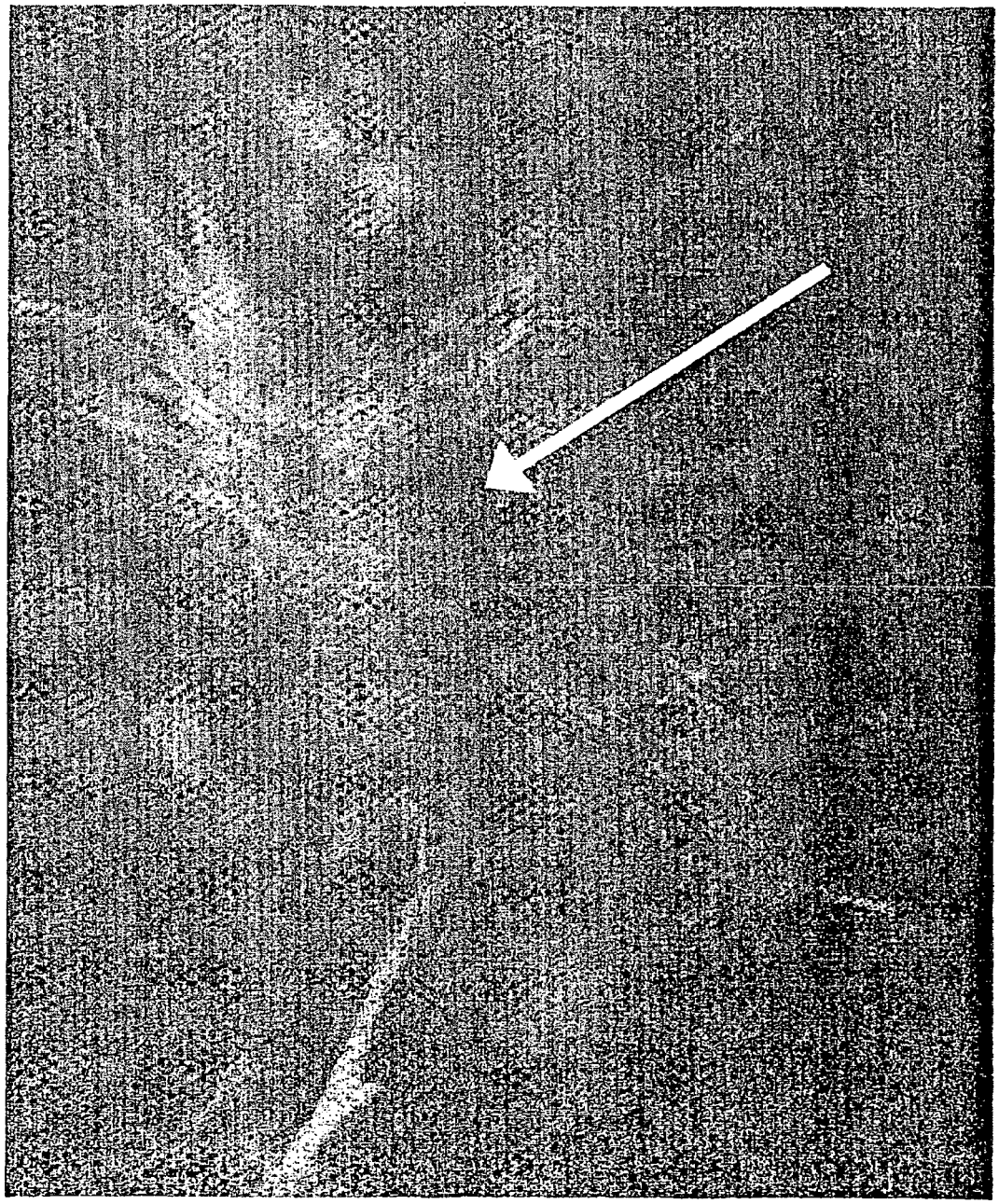
FIG. 14 shows the detection of desmin by ICC in murine ES cells cultured in TGF-beta-1 and FGF-4 for five days on type I collagen and human plasma fibronectin (see Example 6).

After incubating the cells for five days in the presence of the putative differentiation-inducing agents, the cells in the wells were assayed for expression of cell type-associated genes by ICC. Primary antibodies to desmin, nestin, and GATA4 were applied to the cells and visualized by fluorescence microscopy as described in Example 3 above. FIG. 14 shows immunofluorescence from anti-desmin antibody bound to desmin, a marker of mesodermal cell lineages, in murine ES cells cultured in TGF-beta-1 and FGF4 for five days on type I collagen and human plasma fibronectin.

The expression of cell type-associated genes such as GATA4 and nestin by the murine ES cells in the wells that were induced to differentiate was also detected by RT-PCR assay performed as described in Example 2 (data not shown).

Example 7

Screen with Murine Gene-Trap ES Cell Lines; Detection by X-Gal Staining and ICC:

Cells of the murine gene trap ES cell lines K18E2 and M7H7 each have DNA encoding beta-galactosidase inserted as a marker gene in a genetic locus that is activated when the cells differentiate. The DNA encoding beta-galactosidase is inserted in-frame with correct orientation at a site such that it is expressed and beta-galactosidase is produced when the genetic locus in which it is inserted is activated. Accordingly, the beta-galactosidase coding sequence operates as a marker permitting detection of the differentiation of K18E2 and M7H7 ES cells. The beta-galactosidase marker DNA is inserted at different loci in K18E2 and M7H7 ES cells, and the sets of conditions that leads to activation of the marker gene are not the same for the two cell types. The beta-galactosidase marker in K18E2 ES cells is expressed in many early differentiated cell lineages; the beta-galactosidase marker in M7H7 cells is expressed in early mesoderm and retains expression in endothelial and hematopoietic pathways.

Cells of murine gene trap cell lines K18E2 were treated as described in Example 6 above and subsequently stained with X-gal to detect expression of the marker beta-galactosidase gene. X-gal staining is generally well known in the art. Briefly, the cells were washed once with 0.1M phosphate buffer, fixed at room temperature in 25% gluteraldehyde in 0.1M phosphate buffer, washed again five times in phosphate buffer, and stained overnight at 37 degrees C. with X-gal stain. The pH of the buffer was in the range of 7.0-8.0 depending on the cells used.

Figure 15:
FIG. 15 shows the detection of X-gal staining of cells of the murine gene trap ES cell line K18E2 that were cultured for five days on type I collagen and human plasma fibronectin in the presence of TGF-beta-1 and FGF-4 (see Example 7). Detection of expression of the marker beta-galactosidase gene in the gene trap ES cells indicates that the cells were induced to differentiate.

FIG. 15 shows the detection of X-gal staining of K18E2 ES cells that were cultured for five days on type I collagen and human plasma fibronectin in the presence of TGF-beta-1 and FGF-4. Detection of expression of the beta-galactosidase marker gene in cells derived from the K18E2 ES cells indicates that the cells were induced to differentiate.

Figure 16:
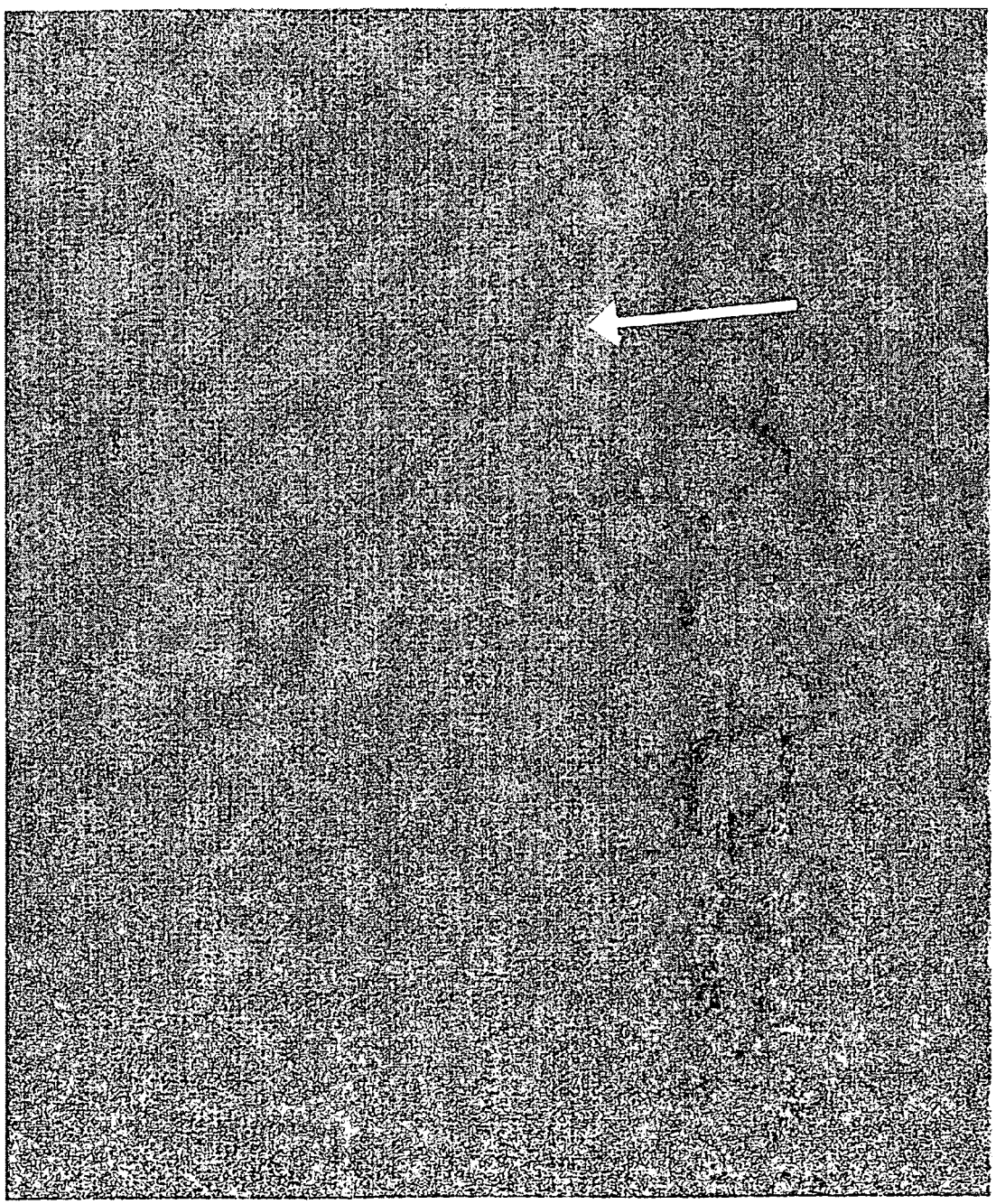
FIG. 16 shows the detection of beta-galactosidase by ICC (using antibody to beta-galactosidase) in cells of murine gene trap ES cell line M7H7 that were cultured for five days on type I collagen and human plasma fibronectin in the presence of TGF-beta-1 and FGF-4. Nuclei are co-visualized by DAPI staining.
Figure 17:
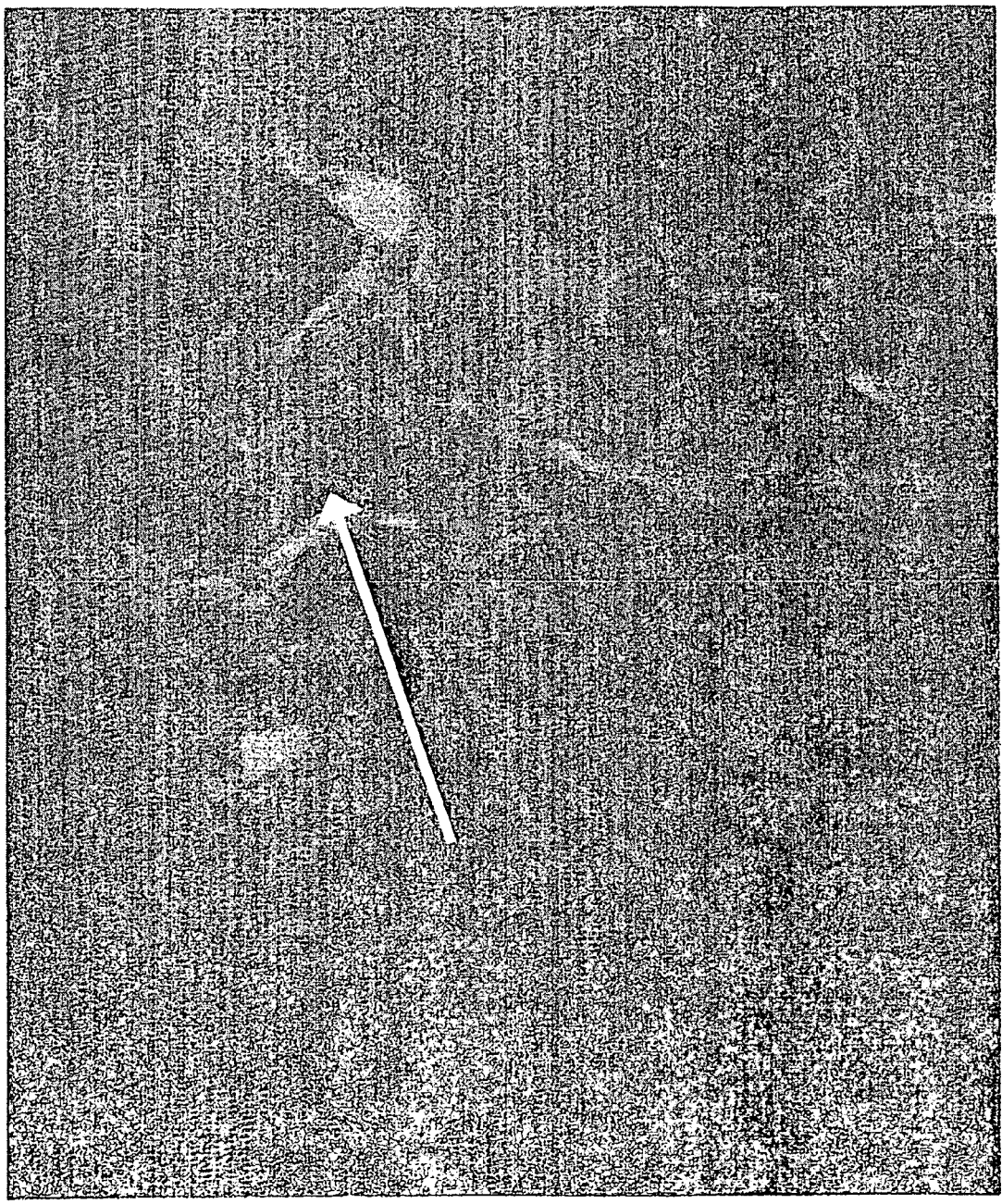
FIG. 17 shows the detection of beta-galactosidase by ICC in cells of murine gene trap ES cell line K18E2 that were cultured for five days on type I collagen and human plasma fibronectin in the presence of FGF-4.

Expression of the beta-galactosidase marker gene in K18E2 and M7H7 ES cells that were cultured in the presence of differentiation-inducing agents was also detected by ICC. FIG. 16 shows the detection of beta-galactosidase by ICC (using antibody to beta-galactosidase) in M7H7 ES cells that were cultured for five days on type I collagen and human plasma fibronectin in the presence of TGF-beta-1 and FGF-4. Cell nuclei were co-visualized by DAPI staining. FIG. 17 shows the detection of beta-galactosidase by ICC in K18E2 ES cells that were cultured for five days on type I collagen and human plasma fibronectin in the presence of FGF-4.

Using RT-PCR to detect expression, the beta-galactosidase marker gene in murine gene trap ES cells was also shown to be activated when the cells were induced to differentiate by other cells (data not shown).

Example 8

Screen for Induction of Differentiation by Cell-Cell Interactions:

Murine gene trap K18E2 and M7H7 ES cells were plated in wells of a 24-well tissue culture plate (5,000 to 20,000 cells/well) and were allowed to differentiate in the presence of FGF4 and TGF-beta-1, generally as described in Example 6 above, except that in some of the wells, the cells were plated onto a layer fibroblast mesenchymal inducer cells. After incubation for five days, the cells were all transferred to wells containing FGF-4 and TGF-beta-1 without inducer cells, and were cultured for an additional five days. Following this treatment, expression of the beta-galactosidase marker gene was detected by the ICC protocol described in Example 3. The images in FIGS. 18-21 are of labeling using monoclonal anti-β-galactosidase (G-6282 Sigma-Aldrich, Inc.) primary antibody and anti-mouse IgM FITC conjugated (F9259 Sigma-Aldrich, Inc.) secondary antibody.

Figure 18:
FIG. 18 shows the presence of β-galactosidase in K18E2 cells that were cultured with FGF-4 and TGF-β1 on inducer fibroblasts for 5 days, then sub-cultured for an additional 5 days with FGF-4 and TGF-β1 alone.
Figure 19:
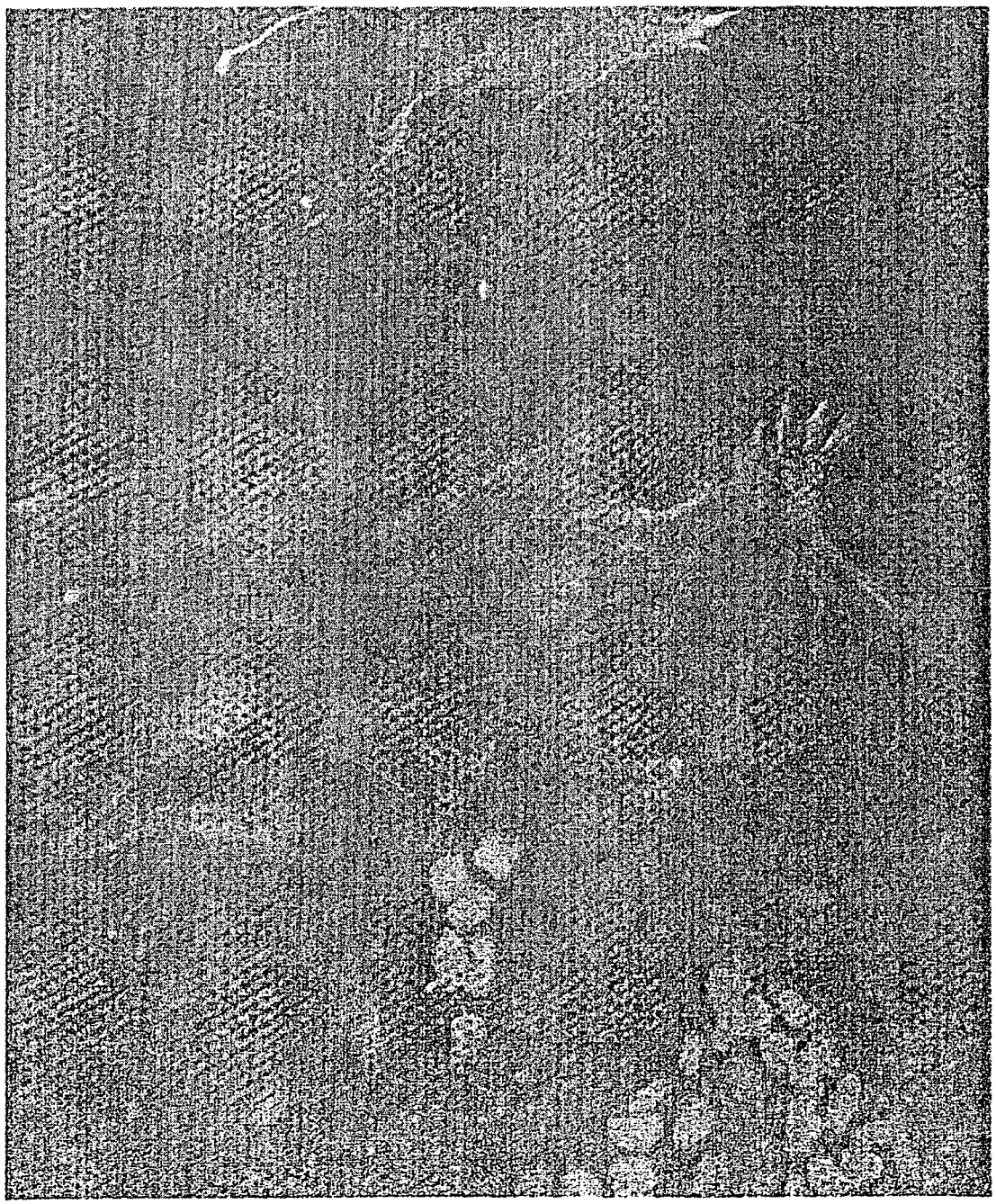
FIG. 19 shows the presence of β-galactosidase in M7H7 cells that were cultured with FGF-4 and TGF-β1 on inducer fibroblasts for 5 days, then sub-cultured for an additional 5 days with FGF-4 and TGF-β1 alone.
Figure 20:
FIG. 20: shows the presence of β-galactosidase in K18E2 cells that were cultured with FGF-4 and TGF-β1 in the absence of inducer fibroblasts, and then sub-cultured for 5 more days in the same conditions.
Figure 21:
FIG. 21 shows the presence of β-galactosidase in M7H7 cells that were cultured with FGF-4 and TGF-β1 in the absence of inducer fibroblasts, and then sub-cultured for 5 more days in same conditions.

Results:

FIG. 18 shows the presence of β-galactosidase in K18E2 cells that were cultured with FGF-4 and TGF-β1 on inducer fibroblasts for 5 days, then sub-cultured for an additional 5 days with FGF-4 and TGF-β1 alone. FIG. 19 shows the presence of β-galactosidase in M7H7 cells that were cultured with FGF-4 and TGF-β1 on inducer fibroblasts for 5 days, then sub-cultured for an additional 5 days with FGF-4 and TGF-β1 alone. FIG. 20 shows the presence of β-galactosidase in K18E2 cells that were cultured with FGF-4 and TGF-β1 in the absence of inducer fibroblasts, and then sub-cultured for 5 more days in same conditions. FIG. 21 shows the presence of β-galactosidase in M7H7 cells that were cultured with FGF-4 and TGF-β1 in the absence of inducer fibroblasts, and then sub-cultured for 5 more days in same conditions.

The beta-galactosidase marker gene was expressed by both lines of gene trap stem cells cultured with FGF-4 and TGF-β1 on inducer fibroblasts, and also by the same stem cells cultured with FGF-4 and TGF-β1 alone. However, the beta-galactosidase marker gene was expressed by the M7H7 cells cultured with FGF-4 and TGF-β1 on inducer fibroblasts significantly more strongly than by the M7H7 cells that were cultured with FGF-4 and TGF-β1 alone. The beta-galactosidase marker gene of M7H7 is activated when the cells are induced to differentiate into cells of the mesodermal lineage, and are therefore useful for identifying conditions that induce the stem cells to differentiate into hematopoietic cells. This example demonstrates the use of the invention to identify cell-cell interactions between stem cells and inducer fibroblasts that operate to induce differentiation of stem cells into cells of the mesodermal lineage, e.g., for producing hematopoietic cells.

Example 9

Directing Differentiation with Multi-Nodal Markers:

This example demonstrates how multi-nodal markers can be used to identify differentiated cell types.

Cell line A is a totipotent gene trap stem cell line with a gene trap marker that is expressed when the cells are exposed to three different sets of conditions that direct them to differentiate, respectively, into heart, lung, and kidney.

Cell line B is a totipotent gene trap stem cell line with a different gene trap marker that is expressed when the cells are exposed to three different sets of conditions that direct them to differentiate, respectively, into lung, brain, and eye.

Cell Types in which the Gene Trap Marker is Expressed

| Cell line A | Cell line B |
|---|---|
| heart | eye |
| lung | lung |
| kidney | brain |

Screening is performed to identify a set of conditions that activates the marker in both cell lines; this set of conditions is expected to direct differentiation to lung.

Example 10

Screening in Eggs:

An array of avian eggs is used as the set of compartments in which screening for differentiation is performed. $10^2$ to $10^5$ totipotent, nearly totipotent, or pluripotent stem cells; e.g., murine or primate ES cells, are introduced into each egg. One or more putative differentiation-inducing agents; e.g., growth factors, cytokines, ECM compounds, and/or inducer cells, are then added to the cells in each egg in various combinations and temporal sequences. The eggs are incubated and activation of cell type-associated genes in the cells is detected by RT-PCR.

The assay can be performed using gene trap ES cells having gene trap markers that are activated when the stem cells differentiate into specific cell types. Use of such cells permits two types of screening to be performed. In one, an array of eggs is prepared with each egg containing the same type of gene trap stem cell, and a different combination of putative differentiation-inducing agents. In the other, an array of eggs is prepared with each egg containing stem cells having a different gene trap marker that is activated when the cell is induced to differentiate, and the same combination of putative differentiation-inducing agents. The first assay is a screen to identify agents or conditions that direct differentiation of stem cells into a specific cell type. The second assay identifies cell type-associated markers that are activated by a particular set of putative differentiation-inducing agents.

Example 11

Screens Utilizing Lineage Tracers Introduced by Site-Specific Recombination:

For efficient detection of the activation of a genetic locus that is only transiently activated at a step or "node" in the branching pathway leading to differentiation to a desired specific cell type, gene trap stem cells can be made by inserting two coding sequences into the genome of the stem cell:

(i) a sequence encoding a recombinase that is inserted into the locus in-frame with correct orientation at a site such that it is expressed and recombinase is produced when the genetic locus in which it is inserted is activated; and (ii) a sequence encoding a marker protein that is disrupted by a nucleotide sequence with flanking recombinase sites that is excised by the recombinase to generate an undisrupted marker gene. This sequence can be inserted into a genetic locus that is constitutively active, or into the same locus as the recombinase DNA.

When the genetic locus in which the recombinase DNA is inserted is activated, recombinase is synthesized and catalyzes excision of the disrupting sequence from the marker DNA sequence, permitting detection of the marker in the differentiated cell. When transcription of the marker DNA is under control of a constitutively active promoter, the marker can be detected even when the locus in which the recombinase DNA is inserted is a transiently activated locus that subsequently becomes deactivated. (See Zinyk et al., Curr. Biol. (1998) 8:665-668; Dymecki et al., Dev. Biol. (1998) 201:57-65, each incorporated by reference in its entirety). For example, the recombinase systems such as that of the λ integrase family can be used to implement this method. The cre-loxP and FLO-FRT systems allow the activation or inactivation of target sequences that operate as permanent markers in the genomes of cells having passed certain points in development. The use of these systems in fate mapping cells in animal development is well known in the art; however, the use of recombinase-mediated cell fate marking for the in vitro screening of stem cell differentiation has not been described. Current fate mapping techniques utilize two components: 1) a recombinase animal that expresses the recombinase (Cre or FLP) in a gene-specific manner, and 2) the indicator animal that has a transgene activated in the presence of the recombinase in a permanent fashion e.g. such that β-gal is expressed in this and all cells derived from such a cell regardless of their differentiated state. This recombinase can be introduced into ES cells in gene trap vectors as described above, and the recombinant ES cells can be used to produce an assortment of individual recombinase mice that can provide a random assortment of gametes harboring many gene trapped recombinase genes. These gametes (sperm or eggs) can then be used with the complementary gamete from the indicator animal to produce embryos, embryoid bodies, or stem cells that leave a permanent marker of having passed a given point in the developmental tree. Such lineage-tracing stem cells have particular utility when the gene of interest is only transiently expressed and therefore difficult to detect. Libraries of stem cells in which such recombinase-based markers are randomly inserted may be made and screened to identify cell type associated gene trap markers. Alternatively, libraries of stem cells in which such recombinase-based markers are targeted to specific loci are useful in the screening assay of the present invention for determining the conditions under which stem cells are induced to express cell type-associated genes and differentiate into a particular cell type.

What is claimed:

1. A method for inducing differentiation of an embryonic stem (ES) cell to form differentiated cells selected from the group consisting of cells of endothelial lineage, and cells of endodermal lineage, the method comprising exposing the ES cell to a tenascin, thereby inducing differentiation of the ES cell.

2. The method of claim 1, wherein said tenascin is selected from the group consisting of: tenascin-C, tenascin-R, tenascin-X, tenascin-Y and tenascin-W.

3. The method of claim 2, wherein said tenascin is tenascin-C.

4. The method of claim 1, wherein said differentiated cells are endodermal precursor cells.

5. The method of claim 3, wherein said differentiated cells are endodermal precursor cells.

6. The method of claim 1, wherein the ES cell is a primate ES cell.

7. The method of claim 3, wherein the ES-cell is a primate ES cell.

8. The method of claim 6, wherein said primate ES cell is a human ES cell.

9. The method of claim 1, wherein said differentiated cells exhibit increased expression of choline acetyltransferase (ChAT).

10. The method of claim 3, wherein said differentiated cells exhibit increased expression of choline acetyltransferase (ChAT).

11. The method of claim 1, wherein said differentiated cells exhibit increased expression of nestin.

12. The method of claim 3, wherein said differentiated cells exhibit increased expression of nestin.

13. The method of claim 1, wherein said differentiated cells exhibit increased expression of GATA-4.

14. The method of claim 3, wherein said differentiated cells exhibit increased expression of GATA-4.

15. The method of claim 1, wherein the concentration of said tenascin is about 50 ng/ml.

16. The method of claim 3, wherein the concentration of said tenascin-C is about 50 ng/ml.

* * * * *